(12) United States Patent
Graham et al.

(10) Patent No.: US 12,025,598 B2
(45) Date of Patent: Jul. 2, 2024

(54) TECHNIQUES FOR ANALYTICAL SYSTEM DATA ACQUISITION

(71) Applicant: WATERS TECHNOLOGIES IRELAND LIMITED, Dublin (IE)

(72) Inventors: Kendon S. Graham, Millis, MA (US); David Gadsby, Rochdale (GB)

(73) Assignee: WATERS TECHNOLOGIES IRELAND LIMITED, Dublin (IE)

( * ) Notice: Subject to any disclaimer, the term of this patent is extended or adjusted under 35 U.S.C. 154(b) by 424 days.

(21) Appl. No.: 17/344,488

(22) Filed: Jun. 10, 2021

(65) Prior Publication Data
US 2021/0389288 A1   Dec. 16, 2021

Related U.S. Application Data

(60) Provisional application No. 63/037,924, filed on Jun. 11, 2020.

(51) Int. Cl.
| | |
|---|---|
| *G01N 30/86* | (2006.01) |
| *G01N 30/16* | (2006.01) |
| *G01N 30/72* | (2006.01) |
| *G01N 30/02* | (2006.01) |

(52) U.S. Cl.
CPC ......... *G01N 30/8696* (2013.01); *G01N 30/16* (2013.01); *G01N 30/7233* (2013.01); *G01N 30/8651* (2013.01); *G01N 30/8675* (2013.01); *G01N 2030/027* (2013.01)

(58) Field of Classification Search
CPC ............... G01N 30/16; G01N 30/7233; G01N 30/8651; G01N 30/8675
See application file for complete search history.

(56) References Cited

U.S. PATENT DOCUMENTS

| | | | |
|---|---|---|---|
| 2016/0268112 A1* | 9/2016 | Yip | H01J 49/004 |
| 2020/0098552 A1* | 3/2020 | Young | H01J 49/00 |

FOREIGN PATENT DOCUMENTS

JP     2003125123 A     4/2003

OTHER PUBLICATIONS

International Search Report and Written Opinion for International application No. PCT/IB2021/055125, dated Sep. 2, 2021, 15 pages.

* cited by examiner

*Primary Examiner* — Manuel A Rivera Vargas
(74) *Attorney, Agent, or Firm* — Goodwin Procter LLP

(57) ABSTRACT

Techniques and apparatus for an analytical data acquisition process are described. In one embodiment, for example, an apparatus may include logic to submit a sample list for acquisition via an instrument system, the sample list comprising a plurality of injections for a mass analysis system, generate a queue element in a queue for the sample list, the queue element representing the plurality of injections of the sample list to be performed by the at least one instrument system, the queue comprising a plurality of queue elements submitted by a plurality of users and to indicate a progress of each of the plurality of queue elements, and perform a control function on at least one of the plurality of queue elements responsive to user input, the control function comprising one of stopping, starting, or editing the at least one of the plurality of queue element. Other embodiments are described.

20 Claims, 30 Drawing Sheets

Sample Submission

Sample List | Queue | Real Time Data

Name of sample list [ ]    Q Search

Item name | Sample type | Replicates | Plate position | Function | Run time

1 | ▶

Submit

☐ Trastuzumab Degradation Folder ⌄

▦ Acquity RDa 4 (Idle) 322 ⌃
System 350 356
Select a system from List ▼

◊Start 352 ◊Stop ⟲Reset
    flow    flow    system
Set to initial Conditions 354

⚗ Trastuzumab ⌄
Method

▦ Sample Trays

Tray 1   Tray 2
Plate type
ANSI 48 - Well 2ml plate ▼

Sample Submission 340

| Sample List 342 | | 344 620 346 Queue Real Time Data | | | | |
|---|---|---|---|---|---|---|
| SampleList_1 602 | | | Search 610 | | | |
| Item name | Sample type ▼ | Replicates ▼ | Plate position | Function | | Run time |
| 1 - | None ▼ | - | - | Equilibrate ▼ | | 5 |
| 2 - | None ▼ | - | - | Condition column ▼ | | 40 |
| 3 Sample A | Blank ▼ | 2 | 1 / A3 | Inject sample ▼ | | 40 |
| 4 Sample B | SST ▼ | 2 | 1 / A4 | Inject sample ▼ | | 40 |
| 5 Sample C | Blank ▼ | 2 | 1 / A5 | Inject sample ▼ | ⎫ | 40 |
| 6 Sample D | Analyte ▼ | 2 | 1 / A6 | Inject sample ▼ | ⎬ 604 | 40 |
| 7 Sample E | Analyte ▼ | 2 | 2 / A1 | Inject sample ▼ | ⎪ | 40 |
| 8 Sample F | Analyte ▼ | 2 | 2 / A2 | Inject sample ▼ | ⎭ | 40 |
| 9 Sample G | Analyte ▼ | 2 | 2 / A3 | Inject sample ▼ | | 40 |
| 10 - | None ▼ | - | - | System shutdown ▼ | | 40 |

☐ Trastuzumab Degradation Folder >

Acquity RDa 4 (Idle) System >

Trastuzumab Method >

Method: Trastuzumab ▼

Sample Trays

Tray 1  Tray 2

Plate type: ANSI 48 - Well 2ml plate ▼

[Submit]

*FIG. 6A*

| | Item name | Item Description | Sample type | Sample position | Replicates | Function | Acquisition method name | Run time (min) | Processing method name |
|---|---|---|---|---|---|---|---|---|---|
| 1 | | | | | | System Preparation | TDM Analysis | 6 | |
| 2 | | | | | | Equilibrate | TDM Analysis | 5 | |
| 3 | | | | | | Condition Column | TDM Analysis | 2 | |
| 4 | TDM19APR2019_001 | Solvent | Blank | 2:A,1 | 1 | Inject Samples | TDM Analysis | 2 | TDM Panel KSG |
| 5 | TDM19APR2019_002 | SST 188765 | System Suitability | 2:A,2 | 1 | Inject Samples | TDM Analysis | 2 | TDM Panel KSG |
| 6 | TDM19APR2019_003 | Solvent | Blank | 2:A,1 | 1 | Inject Samples | TDM Analysis | 2 | TDM Panel KSG |
| 7 | TDM19APR2019_004 | CS Level 1 | Standard | 2:A,3 | 1 | Inject Samples | TDM Analysis | 2 | TDM Panel KSG |
| 8 | TDM19APR2019_005 | CS Level 2 | Standard | 2:A,4 | 1 | Inject Samples | TDM Analysis | 2 | TDM Panel KSG |
| 9 | TDM19APR2019_006 | CS Level 3 | Standard | 2:A,5 | 1 | Inject Samples | TDM Analysis | 2 | TDM Panel KSG |
| 10 | TDM19APR2019_007 | CS Level 4 | Standard | 2:A,6 | 1 | Inject Samples | TDM Analysis | 2 | TDM Panel KSG |
| 11 | TDM19APR2019_008 | CS Level 5 | Standard | 2:A,7 | 1 | Inject Samples | TDM Analysis | 2 | TDM Panel KSG |
| 12 | TDM19APR2019_009 | Solvent | Blank | 2:A,1 | 1 | Inject Samples | TDM Analysis | 2 | TDM Panel KSG |
| 13 | TDM19APR2019_010 | CS QC Low | QC | 2:B,1 | 1 | Inject Samples | TDM Analysis | 2 | TDM Panel KSG |
| 14 | TDM19APR2019_011 | 789632 | Analyte | 2:C,1 | 1 | Inject Samples | TDM Analysis | 2 | TDM Panel KSG |
| 15 | TDM19APR2019_012 | 741236 | Analyte | 2:C,2 | 1 | Inject Samples | TDM Analysis | 2 | TDM Panel KSG |
| 16 | TDM19APR2019_013 | 456324 | Analyte | 2:C,3 | 1 | Inject Samples | TDM Analysis | 2 | TDM Panel KSG |
| 17 | TDM19APR2019_014 | 852367 | Analyte | 2:C,4 | 1 | Inject Samples | TDM Analysis | 2 | TDM Panel KSG |
| 18 | TDM19APR2019_015 | 741258 | Analyte | 2:C,5 | 1 | Inject Samples | TDM Analysis | 2 | TDM Panel KSG |
| 19 | TDM19APR2019_016 | CS QC Low | QC | 2:B,2 | 1 | Inject Samples | TDM Analysis | 2 | TDM Panel KSG |
| 20 | | | | | | Condition Column | TDM Cleanup | 4 | |
| 21 | | | | | | Equilibrate | TDM Store | 4 | |

The highlighted rows have been sent to acquisition 630

This sample is being acquired now 632

Degradation Lot 05APR2019 *702*

(In progress) *704*

⋯

Paul R

Method: Trastuzumab
Injections: acquiring 77 out of 99 injections
Started on: 01 Feb 2019 @ 02:15PM
Folder: Trastuzumab Degradation
Description: Accelerated degradation for Lo... *708*

△ Run  ‖ Pause  ☐ Stop

*730*

---

*715B*

Degradation Lot 05APR2019 *702*

(In progress)

⋯

Paul R

| Metho | Edit batch  *740* |
| Injecti | View injections |
| Starte | |
| Folde | Delete batch |
| Descr | Save results |

△ Ru

| Sample List | | | | | | | | | |
|---|---|---|---|---|---|---|---|---|---|
| Sample Set | | | | | | | | | |
| | Item name | Item Description | Sample type | Sample position | Replicates | Function | Acquisition method name | Run time (min) | Processing method name |
| 1 | | | | | | System Preparation | Steroids Analysis | 8 | |
| 2 | | | | | | Equilibrate | Steroids Analysis | 5 | |
| 3 | | | | | | Condition Column | Steroids Analysis | 4 | |
| 4 | 19APR2019_001 | Solvent | Blank | 1:A,1 | 2 | Inject Samples | Steroids Analysis | 4 | PCOS Panel BWH |
| 5 | 19APR2019_002 | SST 188765 | System Suitability | 1:A,2 | 2 | Inject Samples | Steroids Analysis | 4 | PCOS Panel BWH |
| 6 | 19APR2019_003 | Solvent | Blank | 1:A,1 | 4 | Inject Samples | Steroids Analysis | 4 | PCOS Panel BWH |
| 7 | 19APR2019_004 | CS Level 1 | Standard | 1:A,3 | 2 | Inject Samples | Steroids Analysis | 4 | PCOS Panel BWH |
| 8 | 19APR2019_005 | CS Level 2 | Standard | 1:A,4 | 2 | Inject Samples | Steroids Analysis | 4 | PCOS Panel BWH |
| 9 | 19APR2019_006 | CS Level 3 | Standard | 1:A,5 | 2 | Inject Samples | Steroids Analysis | 4 | PCOS Panel BWH |
| 10 | 19APR2019_007 | CS Level 4 | Standard | 1:A,6 | 2 | Inject Samples | Steroids Analysis | 4 | PCOS Panel BWH |
| 11 | 19APR2019_008 | CS Level 5 | Standard | 1:A,7 | 2 | Inject Samples | Steroids Analysis | 4 | PCOS Panel BWH |

| Sample List | Sample Set | | | | | | | | |
|---|---|---|---|---|---|---|---|---|---|
| | Item name | Acquired date | Item Description | Sample type | Sample position | Function | Acquisition method name | Run time (min) | Processing method name |
| 1 | | | | | | System Preparation | Steroids Analysis | 8 | |
| 2 | | | | | | Equilibrate | Steroids Analysis | 5 | |
| 3 | | | | | | Condition Column | Steroids Analysis | 4 | |
| 4 | 19APR2019_001 | 05JUN2019 08:00:00AM | Solvent | Blank | 1:A,1 | Inject Samples | Steroids Analysis | 4 | PCOS Panel BWH |
| 5 | 19APR2019_001 | 05JUN2019 08:04:00AM | Solvent | Blank | 1:A,1 | Inject Samples | Steroids Analysis | 4 | PCOS Panel BWH |
| 6 | 19APR2019_002 | 05JUN2019 08:08:00AM | SST 188765 | System Suitability | 1:A,2 | Inject Samples | Steroids Analysis | 4 | PCOS Panel BWH |
| 7 | 19APR2019_002 | 05JUN2019 08:12:00AM | SST 188765 | System Suitability | 1:A,2 | Inject Samples | Steroids Analysis | 4 | PCOS Panel BWH |
| 8 | 19APR2019_003 | 05JUN2019 08:16:00AM | Solvent | Blank | 1:A,1 | Inject Samples | Steroids Analysis | 4 | PCOS Panel BWH |
| 9 | 19APR2019_003 | 05JUN2019 08:20:00AM | Solvent | Blank | 1:A,1 | Inject Samples | Steroids Analysis | 4 | PCOS Panel BWH |
| 10 | 19APR2019_003 | 05JUN2019 08:24:00AM | Solvent | Blank | 1:A,1 | Inject Samples | Steroids Analysis | 4 | PCOS Panel BWH |
| 11 | 19APR2019_003 | 05JUN2019 08:28:00AM | Solvent | Blank | 1:A,1 | Inject Samples | Steroids Analysis | 4 | PCOS Panel BWH |
| 12 | 19APR2019_004 | 05JUN2019 08:32:00AM | CS Level 1 | Standard | 1:A,3 | Inject Samples | Steroids Analysis | 4 | PCOS Panel BWH |
| 13 | 19APR2019_004 | 05JUN2019 08:36:00AM | CS Level 1 | Standard | 1:A,3 | Inject Samples | Steroids Analysis | 4 | PCOS Panel BWH |
| 14 | 19APR2019_005 | 05JUN2019 08:40:00AM | CS Level 2 | Standard | 1:A,4 | Inject Samples | Steroids Analysis | 4 | PCOS Panel BWH |
| 15 | 19APR2019_005 | 05JUN2019 08:44:00AM | CS Level 2 | Standard | 1:A,4 | Inject Samples | Steroids Analysis | 4 | PCOS Panel BWH |
| 16 | 19APR2019_006 | 05JUN2019 08:48:00AM | CS Level 3 | Standard | 1:A,5 | Inject Samples | Steroids Analysis | 4 | PCOS Panel BWH |
| 17 | 19APR2019_006 | 05JUN2019 08:52:00AM | CS Level 3 | Standard | 1:A,5 | Inject Samples | Steroids Analysis | 4 | PCOS Panel BWH |
| 18 | 19APR2019_007 | 05JUN2019 08:56:00AM | CS Level 4 | Standard | 1:A,6 | Inject Samples | Steroids Analysis | 4 | PCOS Panel BWH |
| 19 | 19APR2019_007 | 05JUN2019 09:00:00AM | CS Level 4 | Standard | 1:A,6 | Inject Samples | Steroids Analysis | 4 | PCOS Panel BWH |
| 20 | 19APR2019_008 | 05JUN2019 09:04:00AM | CS Level 5 | Standard | 1:A,7 | Inject Samples | Steroids Analysis | 4 | PCOS Panel BWH |
| 21 | 19APR2019_008 | 05JUN2019 09:80:00AM | CS Level 5 | Standard | 1:A,7 | Inject Samples | Steroids Analysis | 4 | PCOS Panel BWH |

*FIG. 7D (Cont.)*

Sample submission

Trastuzumab D... Folder
(Idle) Acquity RDa 4 System
Trastuzumab Method
Method: Trastuzumab
Location: Method Folder
Browse
Sample Trays: ANSI 48-Well 2ml plate

| Sample List | Queue | Real Time Data | | | | |
|---|---|---|---|---|---|---|

Sample Set Name: Degradation Lot 05APR2019
Description: Lorem ipsum dolor sit amet, consectetur adipiscing elit, sed do eiusmod tempor incididunt ut labore et dolore magna aliqua.

| | Item name | Sample type | Replicates ▸ | Plate position | Function | Run time |
|---|---|---|---|---|---|---|
| 1 ☐ | - | None ▸ | - ▸ | - | Equilibrate ▸ | 5 |
| 2 ☐ | - | None ▸ | - ▸ | - | Condition column ▸ | 40 |
| 3 ☐ | Sample A | Blank ▸ | 2 ▸ | 1 / A3 | Inject sample ▸ | 40 |
| 4 ☐ | Sample B | SST ▸ | 2 ▸ | 1 / A4 | Inject sample ▸ | 40 |
| 5 ☐ | Sample C | Blank ▸ | 2 ▸ | 1 / A5 | Inject sample ▸ | 40 |
| 6 ☐ | Sample D | Analyte ▸ | 2 ▸ | 1 / A6 | Inject sample ▸ | 40 |
| 7 ☐ | Sample E | Analyte ▸ | 2 ▸ | 2 / A1 | Inject sample ▸ | 40 |
| 8 ☐ | Sample F | Analyte ▸ | 2 ▸ | 2 / A2 | Inject sample ▸ | 40 |
| 9 ☐ | Sample G | Blank ▸ | 2 ▸ | 2 / A2 | Inject sample ▸ | 40 |
| 10 ☐ | - | None ▸ | - ▸ | - | System shutdown ▸ | 40 |

Submit

Sample submission

- ☐ Trastuzumab D... Folder
- Acquity RDa 4 System
- Trastuzumab Method
- Sample Trays ANSI 48-Well 2ml plate

| Sample List | Queue | Real Time Data |
| --- | --- | --- |

Acquire status: RUNNING

▽ First Batch (In progress) ⊗
User:
Application: Peptide Monitoring
Method: Trastuzumab
Folder: Trastuzumab Degradation
Description: Some description added here ▽ Second Batch (Waiting) ⊗
User:
Application: Peptide Monitoring
Method: Trastuzumab
Folder: Trastuzumab Degradation
Description: Some description added here △ Third Batch (Waiting) ⊗
User:
Application: Sample Submission
Method: Trastuzumab
Folder: Trastuzumab Degradation
Description: Some description added here

| | Item name | Sample type | Replicates | Plate position | Function | Run time |
| --- | --- | --- | --- | --- | --- | --- |
| 1 ☐ | - | None ▼ | - | - | Equilibrate ▼ | 5 |
| 2 ☐ | - | None ▼ | - | - | Condition column ▼ | 40 |
| 3 ☐ | Sample A | Blank ▼ | 2 | 1/A3 | Inject sample ▼ | 40 |
| 4 ☐ | Sample B | SST ▼ | 2 | 1/A4 | Inject sample ▼ | 40 |
| 5 ☐ | Sample C | Blank ▼ | 2 | 1/A5 | Inject sample ▼ | 40 |
| 6 ☐ | Sample D | Analyte ▼ | 2 | 1/A6 | Inject sample ▼ | 40 |
| 7 ☐ | Sample E | Analyte ▼ | 2 | 2/A1 | Inject sample ▼ | 40 |
| 8 ☐ | Sample F | Analyte ▼ | 2 | 2/A2 | Inject sample ▼ | 40 |

*FIG. 7H*

Sample submission

- Trastuzumab D... Folder ›
- Acquity RDa 4 System
- Trastuzumab Method ›
- Sample Trays ANSI 48-Well 2ml plate ›

| Sample List | Queue | Real Time Data | | | | | |
|---|---|---|---|---|---|---|---|
| △ ∥ ☐ | Acquire status: | RUNNING | | | | | |

› First Batch — User:    (In progress)   ⊗
Application: Peptide Monitoring
Method: Trastuzumab
Folder: Trastuzumab Degradation
Description: Some description added here ‹ Second Batch — User:    (Waiting)   ⊗
Application: Peptide Monitoring
Method: Trastuzumab
Folder: Trastuzumab Degradation
Description: Some description added here

| ☐ | Item name | Sample type | Replicates | Plate position | Function | Run time |
|---|---|---|---|---|---|---|
| 1 | - | None | - | - | Equilibrate ▸ | 5 |
| 2 | - | None | - | - | Condition column ▸ | 40 |
| 3 | ☐ Sample A | Blank | 2 | 1 / A3 | Inject sample ▸ | 40 |
| 4 | ☐ Sample B | SST | 2 | 1 / A4 | Inject sample ▸ | 40 |
| 5 | ☐ Sample C | Blank | 2 | 1 / A5 | Inject sample ▸ | 40 |
| 6 | ☐ Sample D | Analyte | 2 | 1 / A6 | Inject sample ▸ | 40 |
| 7 | ☐ Sample E | Analyte | 2 | 2 / A1 | Inject sample ▸ | 40 |
| 8 | ☐ Sample F | Analyte | 2 | 2 / A2 | Inject sample ▸ | 40 |

› Third Batch — User:    (Waiting)   ⊗
Application: Sample Submission
Method: Trastuzumab
Folder: Trastuzumab Degradation
Description: Some description added here

*FIG. 7I*

Sample submission

| | Sample List | Queue | Real Time Data | | | | | |
|---|---|---|---|---|---|---|---|---|
| △ | ‖ □ | Acquire status: RUNNING | | | | | | ⊗ |

∨ First Batch    (In progress)
User:
    Application: Peptide Monitoring
    Method: Trastuzumab
    Folder: Trastuzumab Degradation
    Description: Some description added here

| | Item name | Sample type | Replicates | Plate position | Function | Run time |
|---|---|---|---|---|---|---|
| ⊙ 1 □ | - | None ▼ | - | - | Equilibrate ▼ | 5 |
| ⊙ 2 □ | - | None ▼ | - | - | Condition column ▼ | 40 |
| ⊙ 3 □ | Sample A | Blank ▼ | 2 | 1/A3 | Inject sample ▼ | 40 |
| ⊙ 4 □ | Sample B | SST ▼ | 2 | 1/A4 | Inject sample ▼ | 40 |
| ⊗ 5 □ | Sample C | Blank ▼ | 2 | 1/A5 | Inject sample ▼ | 40 |
| ⊙ 6 □ | Sample D | Analyte ▼ | 2 | 1/A6 | Inject sample ▼ | 40 |
| ⊙ 7 □ | Sample E | Analyte ▼ | 2 | 2/A1 | Inject sample ▼ | 40 |
| ⊙ 8 □ | Sample F | Analyte ▼ | 2 | 2/A2 | Inject sample ▼ | 40 |

∨ Second Batch    (Waiting)    ⊗
User:
    Application: Peptide Monitoring
    Method: Trastuzumab
    Folder: Trastuzumab Degradation
    Description: Some description added here

∨ Third Batch    (Waiting)    ⊗
User:
    Application: Sample Submission
    Method: Trastuzumab
    Folder: Trastuzumab Degradation
    Description: Some description added here Sidebar:
- □ Trastuzumab D... Folder ∨
- ⊞ Acquity RDa 4 System ∨
- ⊙ Trastuzumab Method ∨
- ▦ Sample Trays ANSI 48-Well 2ml plate ∨

*FIG. 7J*

Sample submission

| Sample List | Queue | Real Time Data |

Acquire status: RUNNING

▽ ⫿⫿ ☐

∨ First Batch  ( In progress )  ⊗
User:
 Application: Peptide Monitoring
 Method: Trastuzumab
 Folder: Trastuzumab Degradation
 Description: Some description added here ∨ Second Batch  ( Waiting )  ⊗
User:
 Application: Peptide Monitoring
 Method: Trastuzumab
 Folder: Trastuzumab Degradation
 Description: Some description added here ∨ Third Batch  ( Waiting )  ⊗
User:

---

Pause Queue    ✕

The queue will pause when the current acquisition completes. Nothing is removed from the queue and the acquisition can be resumed.

[ Cancel ] [ Pause ]

---

☐ Trastuzumab D... Folder   ⟩
▦ Acquity RDa 4 System   ⟩
⏱ Trastuzumab Method   ⟩
▦ Sample Trays ANSI 48-Well 2ml plate   ⟩

Sample submission

| | | | | |
|---|---|---|---|---|
| ☐ Trastuzumab D... Folder > | Sample List | Queue | Real Time Data | |
| ⊞ Acquity RDa 4 System > | | Acquire status: | PAUSING | |
| ⏱ Trastuzumab Method > | ▽ ‖ ☐ | | | |
| ⋮⋮⋮ Sample Trays ANSI 48-Well 2ml plate > | ∨ First Batch<br>User: | ( Pausing ) | Application:<br>Method:<br>Folder:<br>Description: | Peptide Monitoring<br>Trastuzumab<br>Trastuzumab Degradation<br>Some description added here | ⊗ |
| | ∨ Second Batch<br>User: | ( Waiting ) | Application:<br>Method:<br>Folder:<br>Description: | Peptide Monitoring<br>Trastuzumab<br>Trastuzumab Degradation<br>Some description added here | ⊗ |
| | ∨ Third Batch<br>User: | ( Waiting ) | Application:<br>Method:<br>Folder:<br>Description: | Sample Submission<br>Trastuzumab<br>Trastuzumab Degradation<br>Some description added here | ⊗ |

Sample submission

| Sample List | Queue | Real Time Data |

Acquire status: RUNNING

☐ Trastuzumab D... Folder >

⌘ Acquity RDa 4 System >

⏱ Trastuzumab Method >

▦ Sample Trays ANSI 48-Well 2ml plate >

△ || ▢

> Second Batch  
User:

(In progress)  ⊗

Application: Peptide Monitoring  
Method: Trastuzumab  
Folder: Trastuzumab Degradation  
Description: Some description added here > Third Batch  
User:

(Waiting)  ⊗

Application: Sample Submission  
Method: Trastuzumab  
Folder: Trastuzumab Degradation  
Description: Some description added here

TECHNIQUES FOR ANALYTICAL SYSTEM DATA ACQUISITION

CROSS-REFERENCE TO RELATED APPLICATION

This application claims priority from and the benefit of U.S. Provisional Patent Application No. 63/037,924 filed on Jun. 11, 2020, the entire content of which is incorporated herein by reference.

BACKGROUND

Mass spectrometry (MS) and/or liquid chromatography-mass spectrometry (LC-MS) analytical systems are capable of providing detailed characterization of complex sample sets, including biological matrices, food and environment (F&E) materials, pharmaceutical compounds, metabolic pathway analyses, and/or the like. A typical mass analysis method may generate a large amount of analytical information. For example, an LC-MS method may generate hundreds or even thousands of spectra, chromatograms, or other forms of analysis information.

Software tools that facilitate access to analytical data and performance of post-acquisition investigations are an important functionality of analytical systems. For example, the ability to draw simple conclusions from new and/or pre-existing data rapidly is a desirable aspect of the perceived usability of LC-MS analytical systems. However, conventional systems operate using difficult and convoluted pathways to data. Accordingly, operators are not able to efficiently access information in an intuitive, straightforward manner regarding the function or performance of their systems, which typically leads inefficiencies, unnecessary re-work, and an overall negative user experience with conventional vendor software platforms.

BRIEF DESCRIPTION OF THE DRAWINGS

FIG. 3 illustrates a user interface according to some embodiments.

FIG. 4 illustrates a user interface according to some embodiments.

FIGS. 5A-5B illustrate user interfaces according to some embodiments.

FIGS. 6A and 6B illustrate user interfaces according to some embodiments.

DETAILED DESCRIPTION

Figure 1:
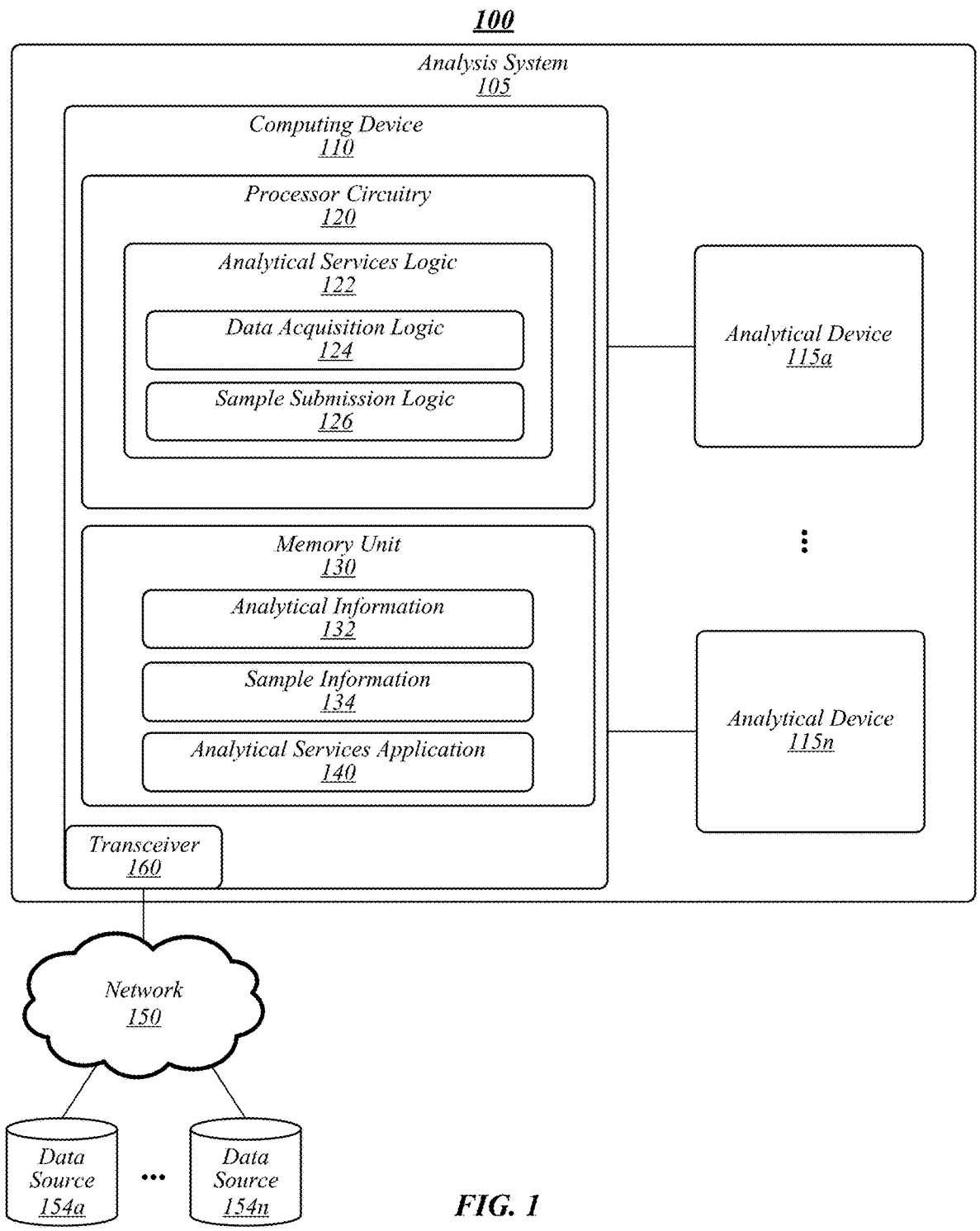
FIG. 1 illustrates an embodiment of a first operating environment.

Various embodiments may generally be directed toward systems, methods, and/or apparatus for an analytical data acquisition process operative to acquire data from an analytical system. In some embodiments, the analytical data acquisition process may be, may include, and/or may interact with a sample submission process operating according to some embodiments to submit samples to the analytical system for analysis. An analytical system may include a mass analysis system, such as a mass spectrometry (MS), liquid-chromatography (LC)-MS (LC-MS) system, ion mobility spectrometry (IMS) system, and/or the like. Although MS or LC-MS systems are described in some examples, embodiments are not so limited, as any analytical system capable of operating according to some embodiments is contemplated herein. In some embodiments, the analytical data acquisition process may provide user interfaces, workflows, operations, functions, processes, and/or the like operative to facilitate the submission of samples to an analytical system, execution of analytical methods, acquisition of analytical data, and/or access to and/or presentation of analytical data.

Analytical systems include a software interface and other tools for operating one or more analytical instruments and access analytical data generated via performance of an analytical method by one of the analytical instruments. The ability to access analytical sytem data and draw simple conclusions from new and/or pre-existing data rapidly is an important aspect of the perceived usability of analytical systems. Difficult and/or convoluted pathways to data that prevent the user from accessing, viewing, and/or understanding simple information regarding the function or performance of their system can lead to frustrations and an overall negative impression of the tools provided by the vendor. Similarly, cursory review of acquired data during the early stages of method development is frequent and necessitates the development of tools that allow users to assess incremental changes to their methods as efficiently as possible.

Analyical data, such as LC-MS data, are frequently described as information rich and are often large relative to the information that the user actually needs to utilize for their experimental purposes. The goal for the user is to obtain accurate and relevant information from the experiments they have performed to plan further experiments, to draw conclusions from data that directly influence their project, and/or determine the status of the analytical instrument used to acquire the data. The user expects that data can be interrogated and presented in such a way that conclusions can be drawn without ambiguity, for example, so that the user is certain of the actions they have taken to examine the data, and that those actions have been performed correctly. For instance, another goal for the user is to use the software tools to gather as much relevant information from their analyses as possible to guide their work by performing comparisons between data files and extracting information from them. However, the complicated and multidimensional nature of certain analytical data, such as LC-MS data, as well as the large volume of information introduces complications and barriers to effective data interpretation using conventional tools and techniques.

Accordingly, some embodiments may provide an analytical data acquisition process operative to allow a simple, efficient path to acquired analytical system data and greater flexibility during the interrogation of acquired LC-MS data. In various embodiments, a analytical data acquisition process may provide software tools that allow a user to extract information and make simple comparisons between experiments more efficiently than capable using conventional platforms. For instance, analytical data acquisition processes according to some embodiments may allow a user to examine and compare data from multiple experiments acquired using different methods and/or data that have been acquired days, weeks, or longer apart. Analytical data acquisition processes according to various embodiments may provide an effective toolset to acquire and investigate data external to currently supported workflows that may operate to enhance the productivity of the analytical instruments in a laboratory or other facility.

Therefore, some embodiments may provide a plurality of technological advantages over conventional systems, including improvements to computing technology. One non-limiting technological advantage may include providing efficient workflows and interfaces to access and compare analytical information, for instance, to facilitate user evaluation of analytical methods, analytical instrument performance, determine experimental conclusions, and/or the like. In this manner, analytical systems using analytical data acquisition processes and associated interfaces according to some embodiments may perform more effectively, improve user efficiency (for instance, less time required to obtain desired information and/or make desired determinations), improve analytical instrument performance (for instance, more effectively and accurately determine instrument operation, functionality, and/or the like), and improved user experience with the software platform interfacing with an analytical instrument. Other technological advantages are described in this Detailed Description.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In the following description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, operating environment 100 may include an analysis system 105 operative to manage analytical data associated with analytical devices 115a-n. In some embodiments, analytical devices 115a-n may be or may include a chromatography system, a liquid chromatography (LC) system, a gas chromatography (GC) system, a mass analyzer system, a mass spectrometer (MS) system, an ion mobility spectrometer (IMS) system, a high-performance liquid chromatography (HPLC) system, a ultra-performance liquid chromatography (UPLC®) system, a ultra-high performance liquid chromatography (UHPLC) system, a solid-phase extraction system, a sample preparation system, a heater (for example, a column heater), a sample manager, a solvent manager, an in vitro device (IVD), combinations thereof, components thereof, variations thereof, and/or the like.

In various embodiments, analysis system 105 may include computing device 110 communicatively coupled to analytical devices 115a-n. Computing device 110 may be operative to communicate with, control, monitor, manage, or otherwise process various operational functions of analytical devices 115a-n. Computing device 110 may obtain analytical information directly via data sources 154a-n and/or directly from analytical devices 115a-n.

In some embodiments, computing device 110 may be or may include a stand-alone computing device, such as a personal computer (PC), server, tablet computing device, cloud computing device, and/or the like. In some embodiments, computing device 110 may be a separate device from analytical devices 115a-n. In other embodiments, computing device 110 may be a part, such as an integrated controller, of analytical devices 115a-n. In various embodiments, computing device 110 may be operative to receive, access, or otherwise obtain analytical information generated via one or more of analytical devices 115a-n.

In some embodiments, an analytical services application 140 may be installed on computing device 110 to manage, control, or otherwise interact with analytical devices 115a-n and/or analytical information generated by analytical devices 115a-n. A non-limiting example of analytical services application 140 may include the UNIFI™ and/or MassLynx™ scientific information system provided by Waters Corporation of Milford, Massachusetts, United States of America. In some embodiments, analytical services application 140 may provide functions, software tools, interfaces, and/or the like accessible from a central hub or other interface of an information system platform, such as UNIFI™. For example, analytical services application 140 may be launched via a selection within a central hub interface of an information system platform. In some embodiments, analytical services application 140 and/or functions thereof (for instance, data acquisition, sample submission, data access, and/or the like) may be implemented as applications or "apps" of an information system platform.

As shown in FIG. 1, computing device 110 may include processing circuitry 120, a memory unit 130, and a transceiver 160. Processing circuitry 120 may be communicatively coupled to memory unit 130 and/or transceiver 160.

Processing circuitry 120 may include and/or may access various logic for performing processes according to some embodiments. For instance, processing circuitry 120 may include and/or may access analytical services logic 122, data acquisition logic 124, and/or sample submission logic 126. Processing circuitry 120, analytical services logic 122, data acquisition logic 124, sample submission logic 126, and/or portions thereof, may be implemented in hardware, software, or a combination thereof. As used in this application, the terms "logic, "component," "layer," "system," "circuitry," "decoder," "encoder," and/or "module" are intended to refer to a computer-related entity, either hardware, a combination of hardware and software, software, or software in execution, examples of which are provided by the exemplary computing architecture 900. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although analytical services logic 122 is depicted in FIG. 1 as being within processing circuitry 120, embodiments are not so limited. In addition, although data acquisition logic 124 and sample submission logic 126 are depicted as being a logic of analytical services logic 122, embodiments are not so limited, as although data acquisition logic 124 and sample submission logic 126 may be separate logics and/or may not be standalone logics but, rather, a part of analytical services logic 122. For example, analytical services logic 122, and/or any component thereof, may be located within an accelerator, a processor core, an interface, an individual processor die, implemented entirely as a software application (for instance, analytical services application 140) and/or the like. Data acquisition logic 124 may operate to perform data acquisition functions according to some embodiments. Sample submission logic 126 may operate to perform sample submission functions according to some embodiments.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store an analytical services application 140 that may operate, alone or in combination with analytical services logic 122, to perform various functions according to some embodiments.

In various embodiments, analytical services application 140 may operate to perform, execute, implement, support, or otherwise facilitate analytical data acquisition processes and/or data submission processes according to some embodiments. In some embodiments, for example, analytical services application 140 may provide graphical user interface (GUI or UI) objects, screens, pages, windows, and/or the like for facilitating information assessment processes (see, for example, FIGS. 3-8).

In some embodiments, memory unit 130 may store analytical information 132. In various embodiments, analytical information 132 may also be accessed via data sources 154a-n. Analytical information 132 may include information associated with operation of analytical devices 115a-n, including, without limitation, raw analytical results, processed analytical results (for instance, spectra, chromatograms, and/or the like), operational information associated with analytical devices 115a-n (for instance, quality control information, pressures, temperatures, device (for example, pumps, valves, and/or the like) functionality, status, and/or the like), and/or the like. In some embodiments, analytical information 132 may include information from a pre-existing analysis. In some embodiments, analytical information 132 may include a data stream, such as a live or substantially live data stream from an analytical instrument, server, network, and/or the like In various embodiments, sample information 134 may include information associated with samples submitted for analysis to analytical devices 115a-n. For instance, sample information 134 may include information associated with a sample list for an MS analytical system. In various embodiments, sample information 134 may include a sample name, sample type, sample function, lot number, injection list, sample list, and/or the like.

In various embodiments, analytical services application 140, via data acquisition logic 124 and/or sample submission logic 126, may allow a user to launch a data acquisition process (for instance, that includes a sample submission process) for one or more of analytical devices 115a-n that may allow a user to follow one or more workflows to acquire, process, and/or view analytical information 132. For example, a data acquisition process may allow a user to select an analytical device 115a-n, that will be used to acquire analytical information 132, specify an acquisition method, prepare the analytical device 115a-n for use, specify sample information 134 (for instance, for an LC-MS system, specify a plate type, tray position, autosampler information, and/or the like; injection list; and/or the like), specify a processing application, specify a processing method, submit samples (for instance, an injection list) to a queue, monitor the progress of items in the queue, control items in the queue (stop, pause, delete, resume, and/or the like), view analytical information 132 in real-time or substantially real-time, view pre-existing analytical information 132, and/or the like. Embodiments are not limited in this context.

In some embodiments, analytical services application 140, for example, via sample submission logic 126, may allow a user to launch a sample submission process. For example, a user may generate and submit a sample or injection list (for instance, with a number of fields that are necessary for acquisition of data, including, without limitation, a sample identifier, sample location and an acquisition method). When the sample list (or injections) are submitted, a sample set may be generated for a queue that provides a central location for all acquisitions to be managed (for example, irrespective of the application or "app" from which they originated). In some embodiments, the queue may hold information necessary for acquisition (for instance, no targets, processing methods or other ancillary information) and a "tag" that denotes the origin app for the sample set. Data may be available in real-time for processing by analytical services application 140, or apps associated with analytical services application 140, and queued items may be edited via selection from the queue and modified in the apps. Automatic execution of processing may be managed by notification from the queue to the apps, for example, indicating that the sample set/injection is ready for processing. In some embodiments, data may be application independent, for example, data acquired through one app may be accessed, processed, and/or the like using another app. Embodiments are not limited in this context.

Figure 2A:
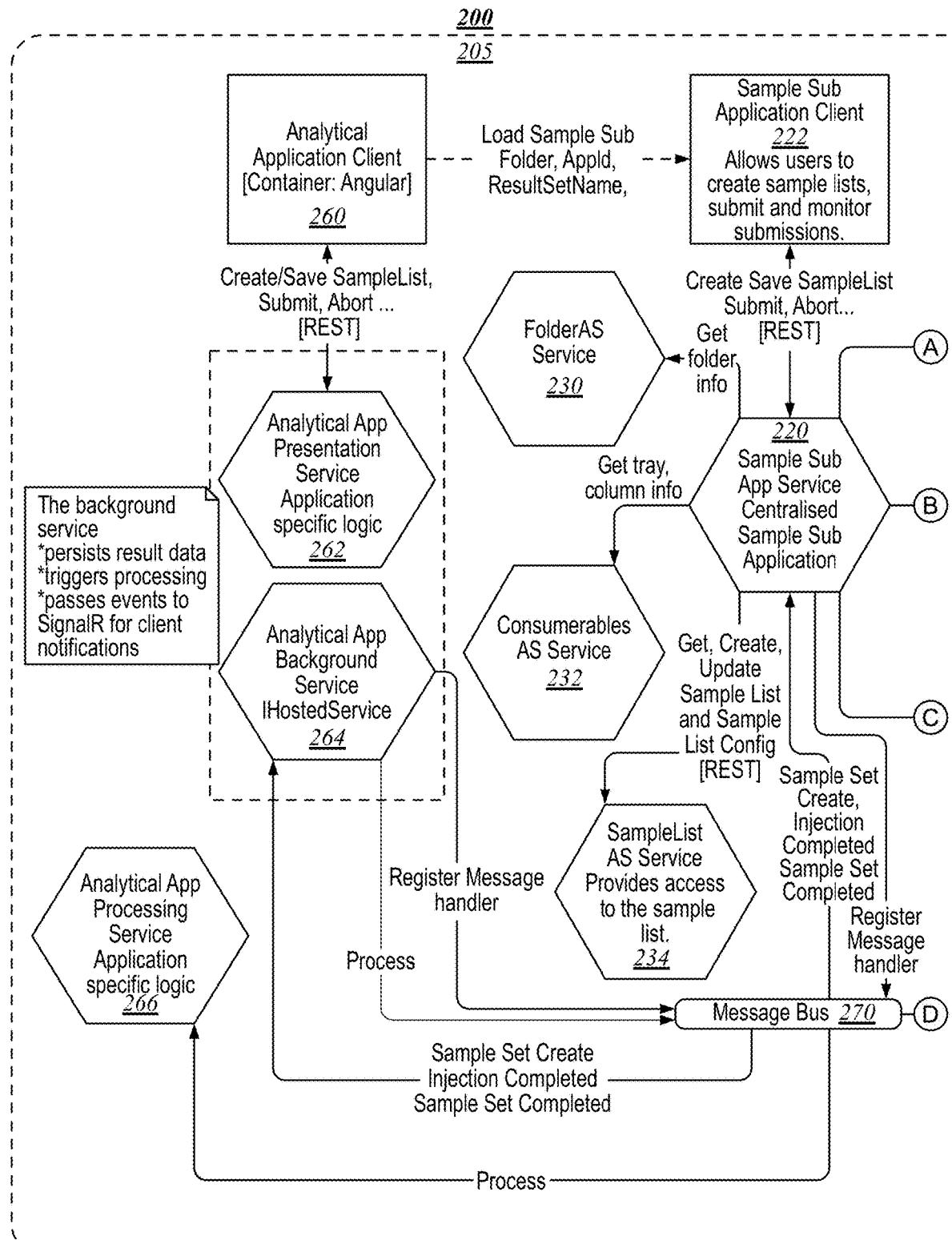
FIGS. 2A-2B illustrate an embodiment of a second operating environment.
Figure 2B:
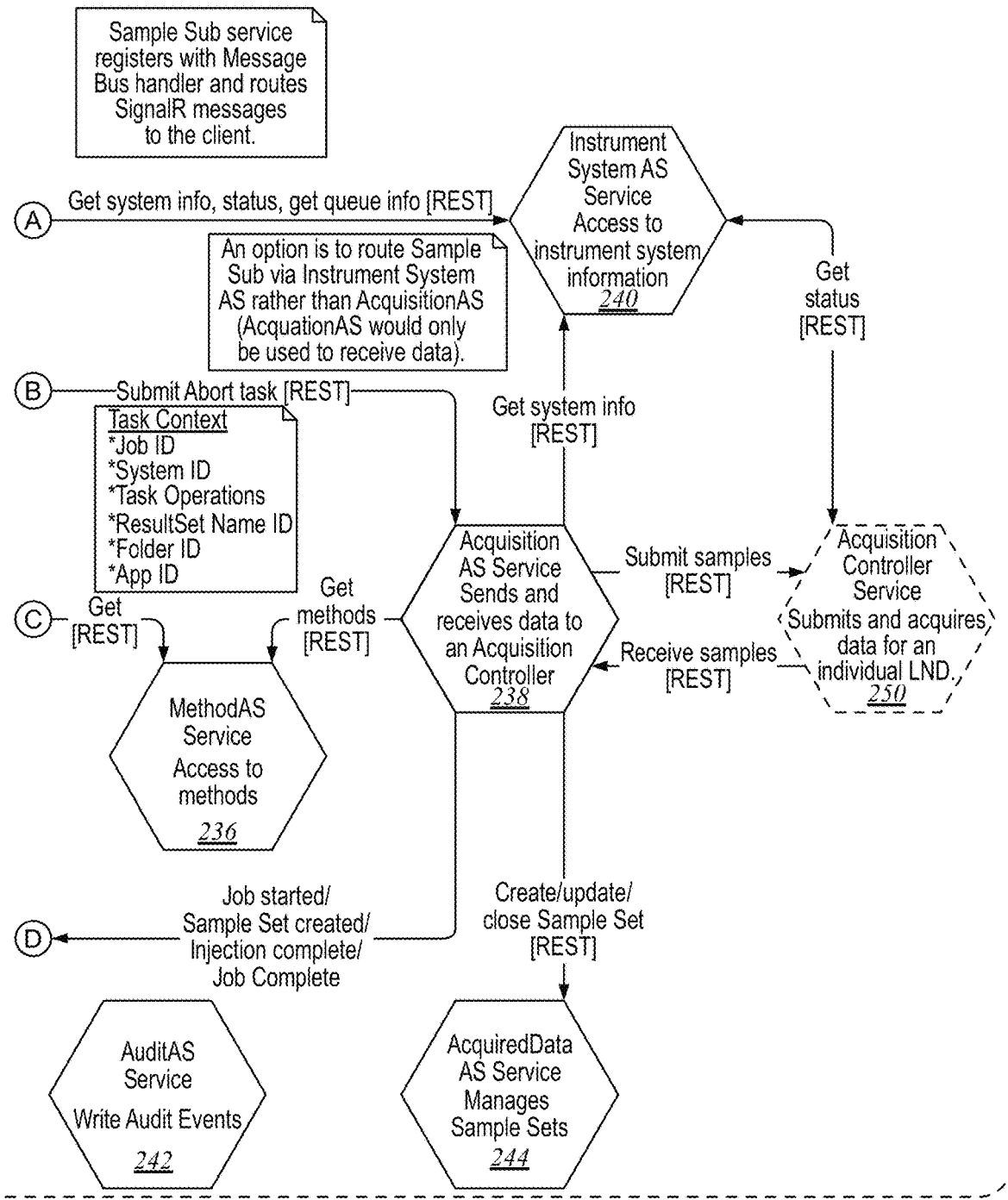

FIGS. 2A-2B illustrate an example of an operating environment 200 that may be representative of some embodiments. As shown in FIGS. 2A-2B, operating environment 200 may include an analytical services application 205 having a structure of service interactions between an analytical application (for instance, an application or portion thereof associated with data acquisition logic 124) and a sample submission application (for instance, an application or portion thereof associated with submission logic 126). In some embodiments, analytical services application 205 may be or may be associated with analytical services application 140 and/or portions thereof operative to perform functions according to some embodiments.

For example, analytical services application 205 may include an analytical application client 260 operative to perform analytical functions according to some embodiments (for instance, data acquisition functions the same or similar to those performed via UNIFI™ MassLynx™, and/or similar systems) and a sample submission application client 222 operative to perform sample submission processes according to eoms embodiments. For example, sample submission application client 222 for an LC-MS system may allow a user to create sample lists, submit samples, and monitor submissions.

In exemplary embodiments, analytical application client 260 may be associated with various services, including, without limitation, a presentation service 252, a background service 264, and/or a processing service 266. In some embodiments, sample submission application client 222 may be associated with certain services, including, without limitation, a sample submission service 220 configured, for example, as a centralized sample submission application.

Analytical application client 260 and sample submission application client 222 may interact via various services. Illustrative and non-restrictive examples of such services may include folder-as-a-service 230, consumables-as-a-service 232, sample list-as-a-service 234, methods-as-a-service 236, acquisition-as-a-service 238, instrument system-as-a-service 240, audit-as-a-service 242, acquired data-as-a-service 244, an acquisition controller service 250, and/or the like. In some embodiments, analytical application client 260, sample submission application client 222, and/or associated services may communicate, at least in part, via a message bus 270.

Figure 3:
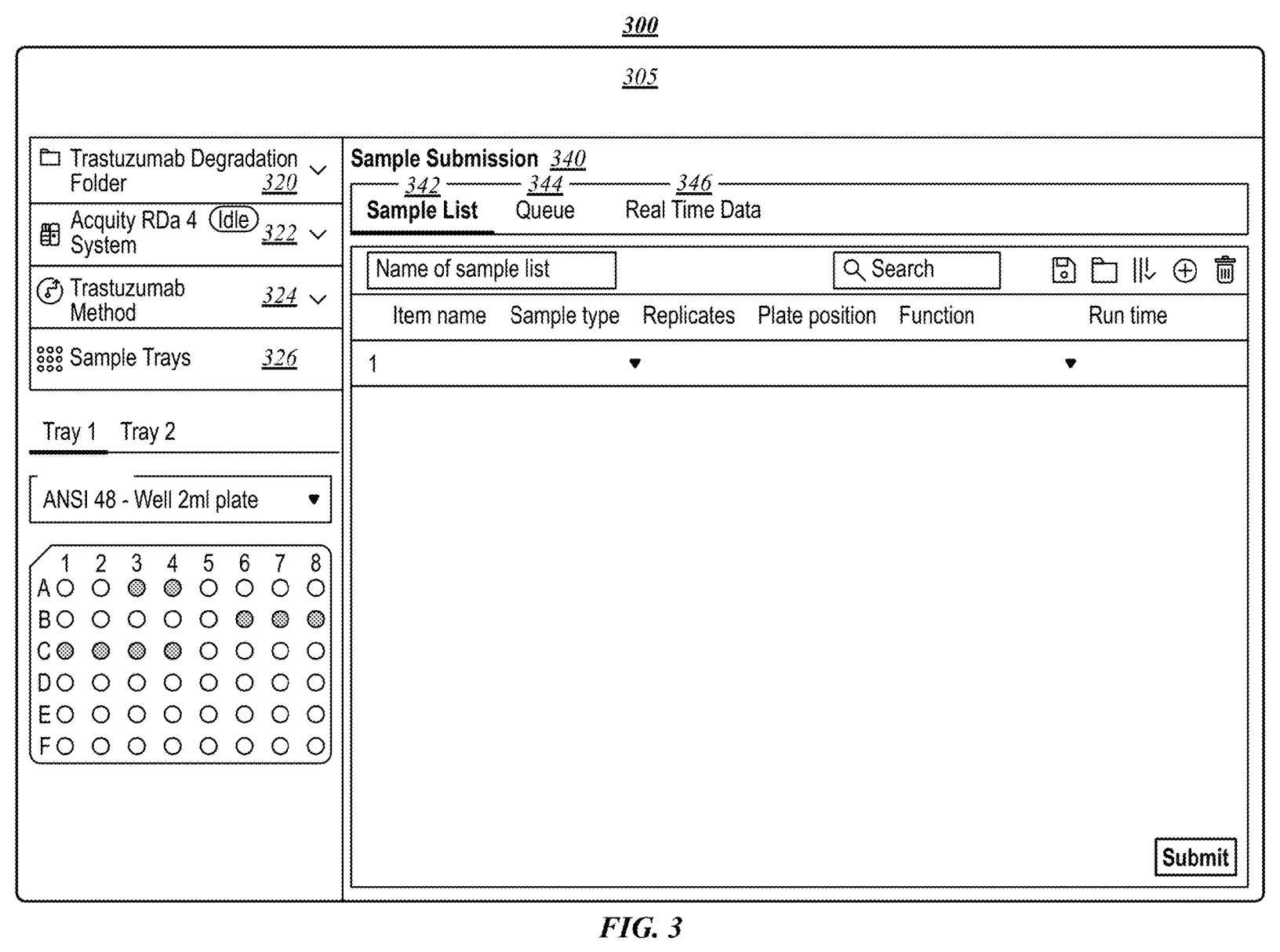

FIG. 3 illustrates an example of an operating environment 300 that may be representative of some embodiments. As shown in FIG. 3, operating environment 300 may include an analytical services screen 305 according to some embodiments. Analytical services screen 305 may include various GUI objects for implementing analytical data acquisition processes according to some embodiments. For example, analytical services screen 305 may present a folder selection object 320 operative to allow a user to select a storage location (for instance, "folder") for storing data. For example, when a user accesses analytical services screen 305 (for instance, as a sample submission app), they may need to see what context the data they are going to acquire is in. For instance, the user may need to know which folder the data will be stored in, and some other metadata that provides an association of the data with another application, or reason the data are being acquired. For example, if a user accesses the sample submission app from a centralized hub, the user may be acquiring data without knowledge of how the data will be processed. It may, for example, be acquired and subsequently examined or processed via another app. Accordingly, a user may choose or define a new folder for the data to be acquired into and optionally add some metadata, for example, that describes the purpose for acquiring the data. In some embodiments, when analytical services screen 305 is accessed from another application, analytical services screen 305 may display the folder that the analysis or study represents and/or an analysis description to the user. For example, folder selection object 320 may have the ability to show a folder name (for instance, where the data is being stored), the application for which the data is being acquired (for example, "Application: Sample Submission," "Application: Peptide Monitoring," and/or the like), and/or any analysis or study names associated with the instance of analytical services screen 305.

In some embodiments, analytical services screen 305 may present a system selection object 322 operative to allow for selection of a system to perform an analysis. FIG. 4 illustrates an example of an operating environment 400 that may be representative of some embodiments. More specifically, FIG. 4 depicts analytical services screen 405 with system selection object 322 in an expanded form, for instance, responsive to selection of system selection object 322. As shown in FIG. 4, system selection object 322 may include a system selection element 350 to select a system, system operation objects 352, a system reset object 354, and/or a system status object 356. System operation objects 352 may allow a user to operate certain aspects of a selected system, including, without limitation, starting a system and/or aspects thereof (for instance, the flow of a system (starting, stopping, or otherwise controlling a flow-control pump)), stopping a system and/or aspects thereof, resetting a system, and/or the like. System reset object 354 may allow a user to set a selected system back to initial conditions, for example, in some embodiments, passes information from the selected method to the instrument hardware, and establishe the initial conditions defined in the method (for instance, temperatures, pump flow rate, detectors ON/OFF, and/or the like). System status object 356 may allow a user to see the status of a selected instrument, such as running, stopped, idle, in error condition, and/or the like.

Figure 5A:
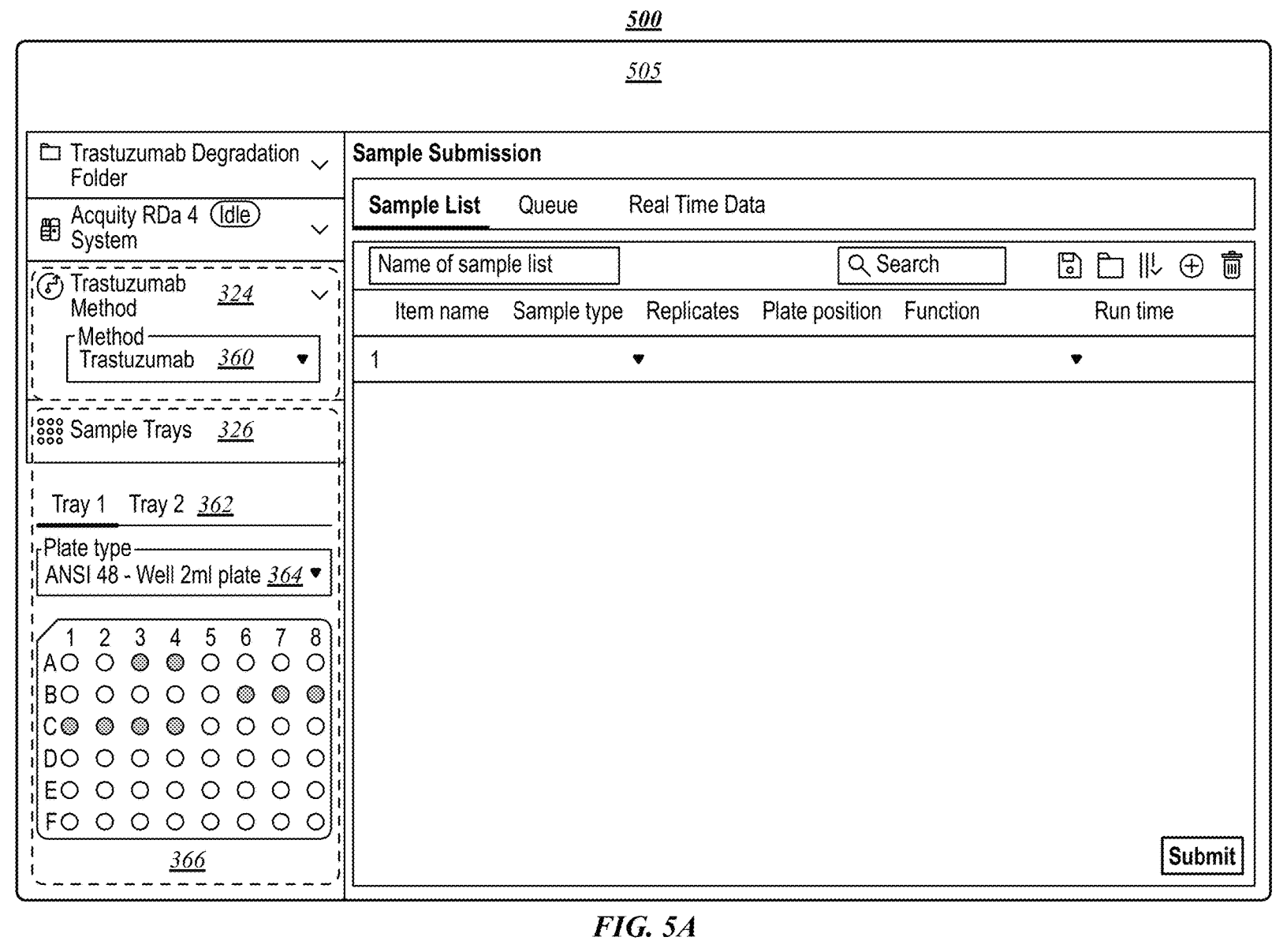

In some embodiments, analytical services screen 305 may present a method selection object 324 operative to allow for selection of a method to be performed. FIG. 5A illustrates an example of an operating environment 500 that may be representative of some embodiments. More specifically, FIG. 5A depicts analytical services screen 505 with method selection object 324 in an expanded form, for instance, responsive to selection of method selection object 324.

As shown in FIG. 5A, selection of method selection object 324 may allow for presentation of a method selection element 360 to select an available method. For example, once system preparation activities have been performed, the user may provide a method (for instance, an acquisition method) to the instrument system, for instance, so that initial conditions can be established before (reliable) acquisition of data can begin. In some embodiments, the method selection element 360 may allow the user to select an acquisition method, for example, from the folder that has been created/defined using folder selection object 320 and/or analytical services screen 305. In various embodiments, acquisition methods may be defined using a method editor app, and may be stored in a folder associated with the instance of the analytical services screen 305 (for example, operating as a sample submission app), for example, for the method to be able to be selected.

Referring to FIG. 3, analytical services screen 305 may include a sample carrier object 326 operative to allow user interaction with sample carriers (for instance, trays) associated with an analytical method, analytical device, and/or the like. In general, a carrier may include an object configured to contain the (liquid) samples to be provided to an analytical device, such as a sample tray for an LC system. As shown in FIG. 5A, sample carrier object 326 may include a carrier selector element 362 (for instance, for a system having a plurality of carriers), a sample type element 364 for selecting a type of carrier, and a carrier display element 366 for displaying aspects of the carrier, such as sample wells, full sample wells, empty sample wells, and/or the like. Other sample carrier definitions may include the physical size of the carrier, well positions, well depth (for instance, expected needle depth), well labelling, fill sequence, and/or the like.

Figure 5B:
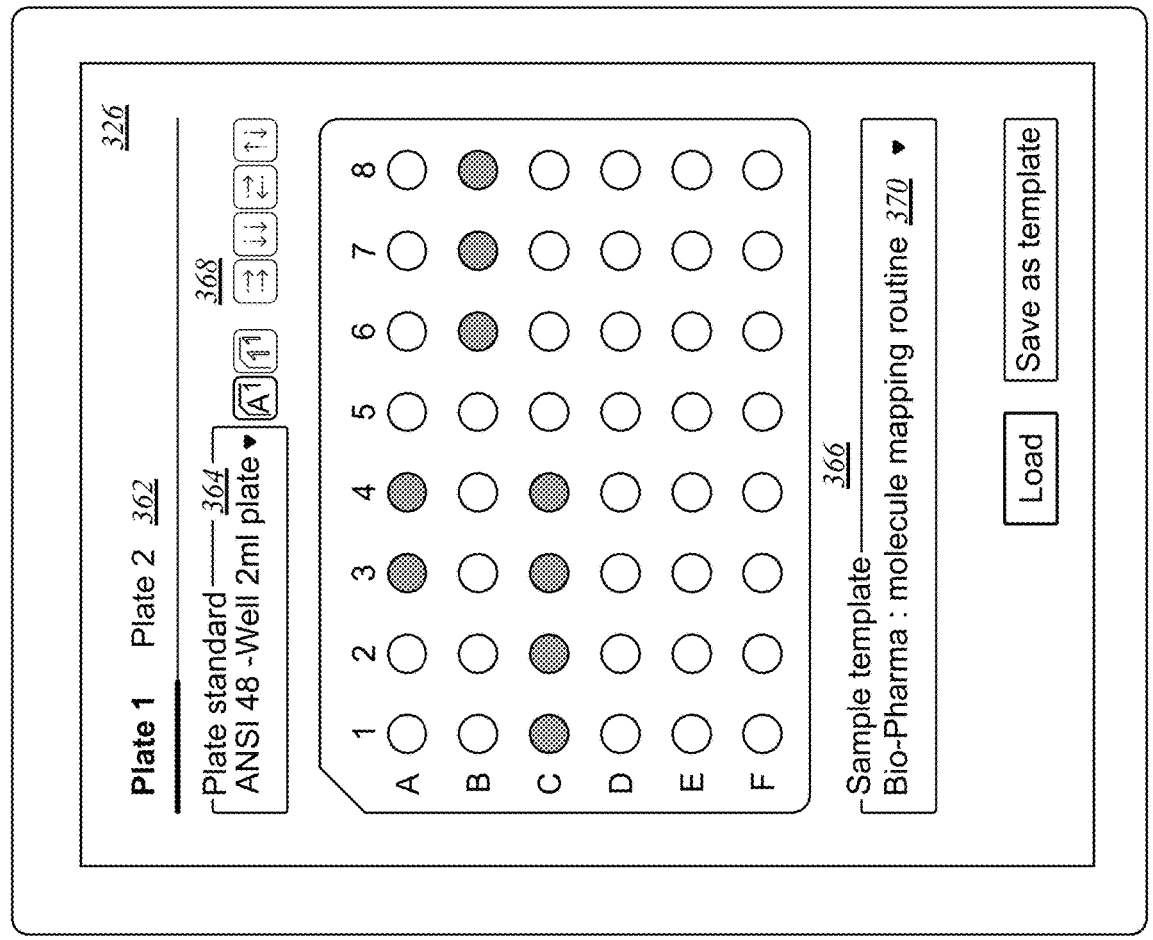
Figure 7M:
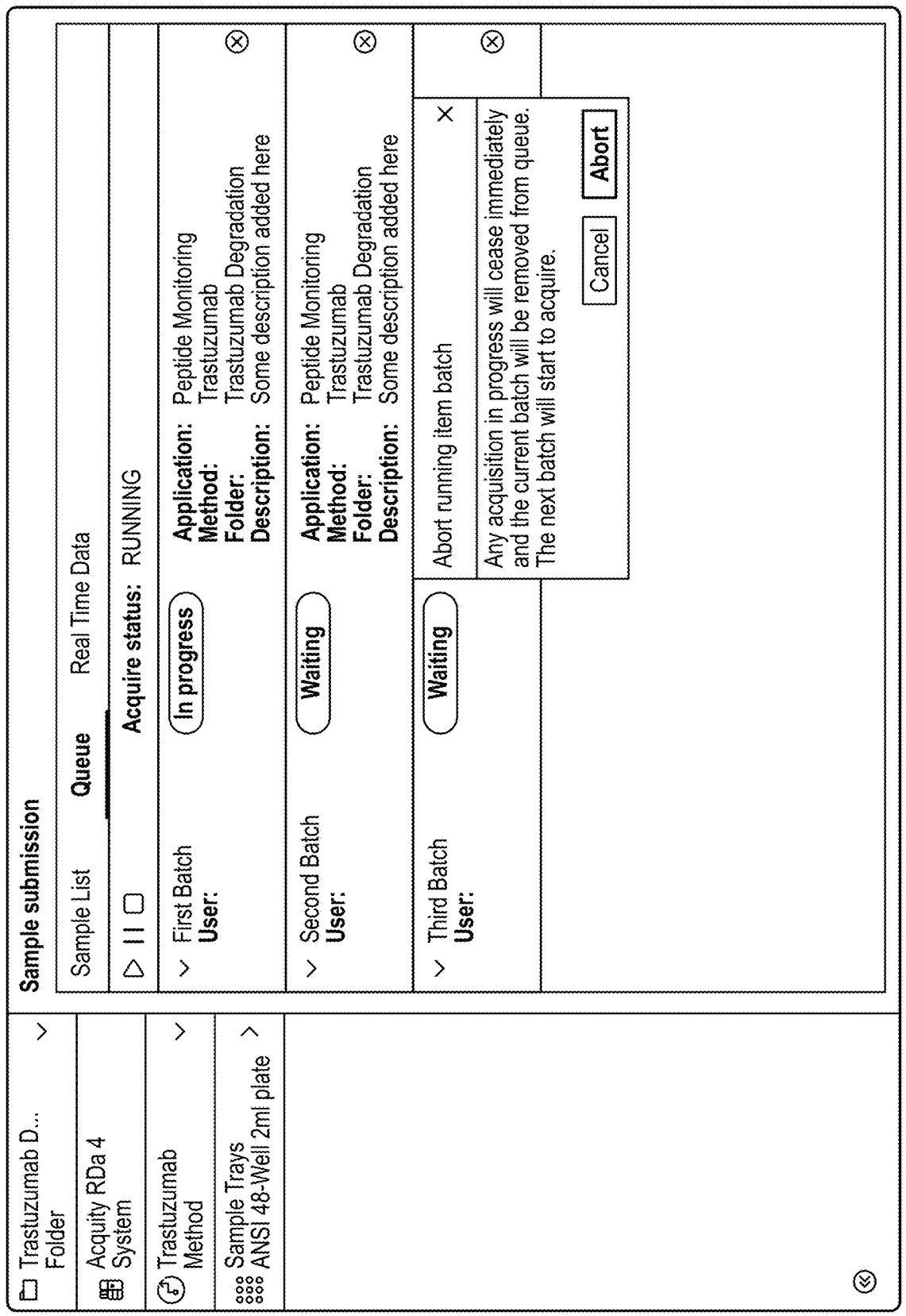
FIG. 7A-7Q illustrate user interfaces according to some embodiments.
Figure 7N:
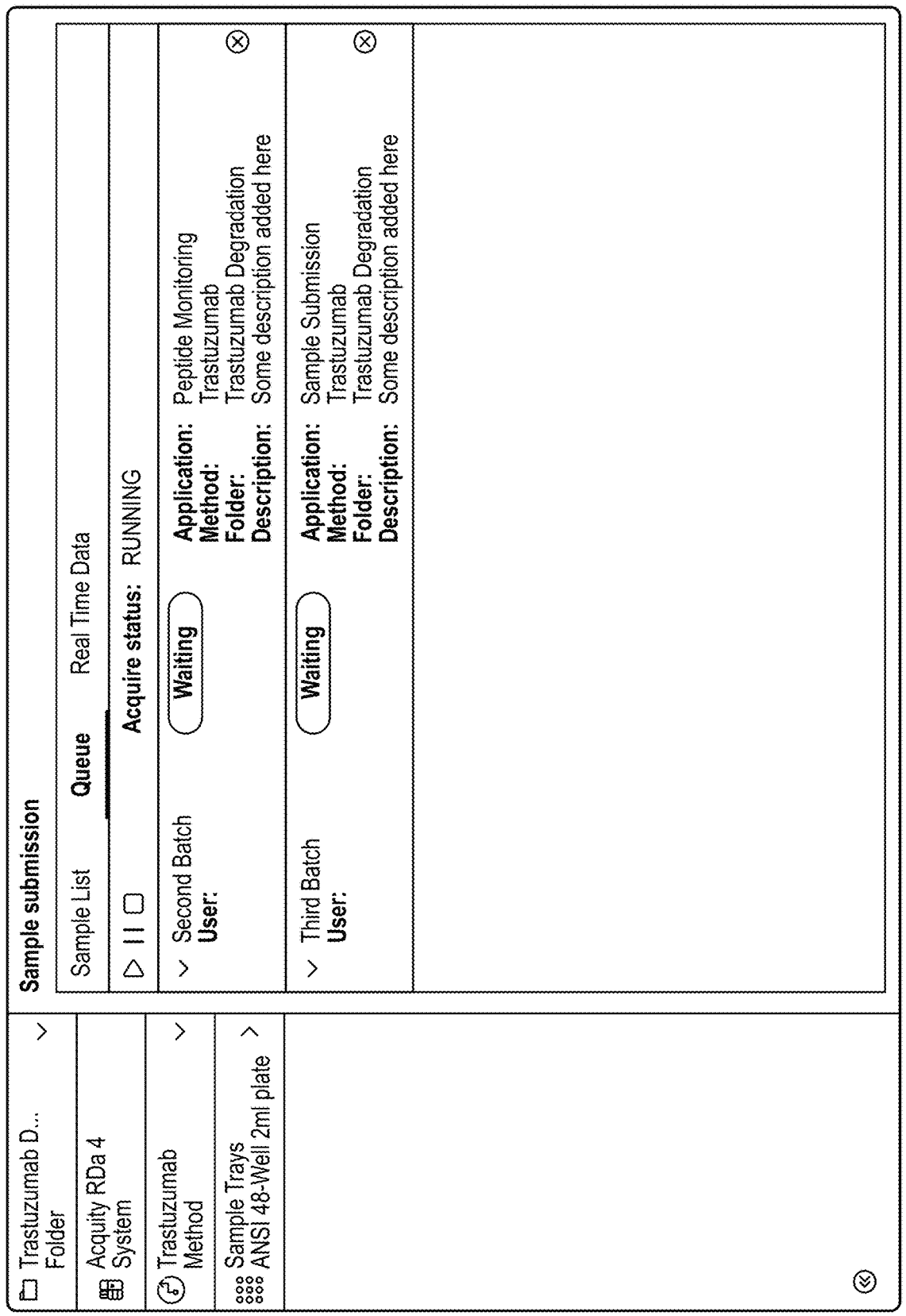
Figure 70:
Figure 7P:
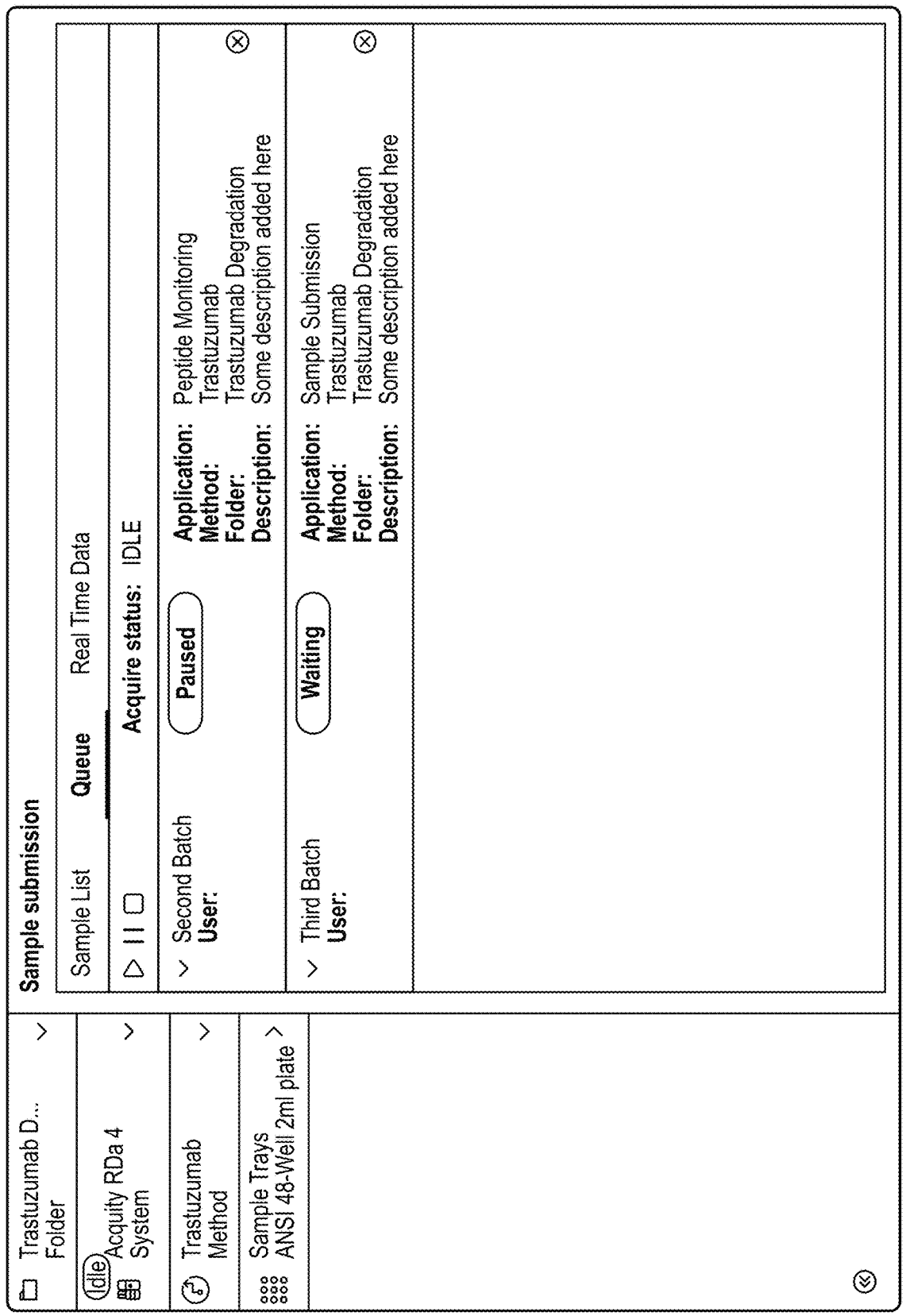

FIG. 5B depicts operating environment 500 with an alternative embodiment of sample carrier object 326. As shown in FIG. 5B, sample carrier object 326 may include configuration element 368 to configure the orientation and/or row configuration for a selected sample carrier. In some embodiments, sample carrier object 326 may include a template element 370 to select a template to use for a selected sample carrier.

In some embodiments, sample carrier object 326 may allow the user to choose the sample carriers, sample carrier positions (for instance, trays in an autosampler bed), and provide an indication of the well positions that are to be used by an associated sample or injection list. In various embodiments, as well positions are entered into an injection list, the presentation of sample carrier 366 may be updated, for example to correlate the well positions that are filled with samples in the physical sample carrier. In some embodiments, types of sample carriers and/or characteristics thereof may be determined based on analysis type and/or characteristics of the analysis (for instance, instrument type, and/or the like).

In some embodiments, sample (well) positions may be added to a sample or injection list. For example, an injection list may include samples A and B and specify that sample A is to be in well A1 (row A, column 1) and sample B is to be in well F3. In various embodiments, a user may define sample (well) positions to be added to an injection or sample list, for example, using sample carrier object 366. In exemplary embodiments, via sample carrier object 366, a user may set a sequence and/or ordering of sample, well, or vial positions when completing an injection or sample list, which may apply, for example, to a fill series in the injection or sample list. In various embodiments, via sample carrier object 366, a user may select an array or other sequence of sample positions, for example, to add to the injection or sample list. For example, a sequence may include a fixed fill sequence, a "horizontal, discontinuous" sequence, a user-defined sequence, and/or the like. In some embodiments, one or more well positions may be automatically selected, for instance, if not specified in a sample list or otherwise indicated for automatic selection. For example, the next available well may be selected.

FIGS. 6A and 6B illustrates an example of an operating environment 600 that may be representative of some embodiments. More specifically, FIG. 6A depicts analytical services screen 605 depicting a sample list 604. In some embodiments, analytical services screen 605, as well as other screens, may provide a sample submission form 340 for managing various aspects of sample management. Sample submission form 340 may include selection objects for sample list 342, queue 344, and real time data 346. Sample list form 610 may be displayed responsive to selection of sample list 342. From sample list form 610, a sample list may be loaded, generated, edited, and/or the like. For example, as depicted in FIG. 6A, sample list "SampleList_1" 602 may be loaded, for instance, from a selected folder (specified via folder selection object 320), and sample list 604 may be displayed. In exemplary embodiments, various elements of sample list 604 may be added, removed, edited, and/or the like via sample list form 610. In general, a sample list allows a user to label their samples conveniently (give the sample a name, for example), define how the data needs to be processed, providce the purpose the sample in the experiment using a sample type, and/or the like. Additional columns or parameters may be added to the sample list that provide information needed by the processing method for each sample, such as concentration or level for standards for individual parameters in a corresponding acquisition method.

In some embodiments, rows, samples, injections, and/or the like defined in sample list 604 may include different methods. In this manner, a single sample list 604 may be used to allow comparison of results by changing method conditions, or simply running appropriate methods for each sample in sample list 604.

In some embodiments, a sample list may be submitted for execution or acquisition. In various embodiments, when the sample list, or a portion thereof, is submitted for acquisition, the information joins a queue (see, for example, FIGS. 7A and 7B). Each item in the queue (for instance, a batch of samples) may represent a row or rows in the sample list that are waiting to be acquired or are being acquired. In various embodiments, items from the same sample list may form a same sample set. In some embodiments, items from the same sample list may form the same sample set despite, for example, being submitted as multiple items in a queue. In various embodiments, information in a sample list that has been submitted to a queue may be edited, including those items for which acquisition has started.

In exemplary embodiments, a user may select an entire sample list or a portion thereof (for instance, one or more rows) to be submitted to a queue. In various embodiments, rows from a sample list that do not contain required information may be prevented from being submitted for acquisition, for instance, from being submitted to a queue. Non-limiting examples of required information may include an item name, sample type, replicate number, plate position, function, run time, and/or the like.

In various embodiments, each row in sample list 604 may operate to tie together sample information, acquisition, and processing information, and/or the like. When data are acquired corresponding to a sample list to form a sample set, the number of rows in the sample set can differ from the number rows in the corresponding sample list, for example, due to replicate injections. For example, if one row in sample ist 604 has "3" replicates specified, this represents 3 rows in a corresponding sample set, one row for the data for each replicate injection. In some embodiments, the columns of a sample list may represent different information types required for the acquisition and processing systems as well for labelling and definition purposes.

In various embodiments, once sample list 604 has been created or loaded from a folder, samples in sample list 604 may be sent to a queue. In some embodiments, the entire sample list 604 may be sent to a queue. In other embodiments, selected samples of sample list 604 may be sent to a queue. For example, a user may select the entire sample list 604 or portions thereof, then select a "submit" function to submit the selected items to the queue. In some embodiments, a user may re-submit at least a portion of sample list 604, which may become a different item(s) in a queue (i.e., first samples of the first submission and second samples (which may be or may include some of the first samples) the second submission may be separate items in a queue). In some embodiments, a queue indicator 620 may operate to indicate various information regarding a queue, such as a number of items in a queue, queue status, and/or the like.

Referring to FIG. 6B, therein is depicted sample list 614 where at least a portion thereof has been submitted to a queue. Certain rows may be highlighted 630 to indicate a status of the samples associated therewith, for example, that the samples have been sent to a queue and/or to acquisition. In another example, a row may be highlighted 632 to indicate that the sample associated therewith is currently being acquired.

In various embodiments, samples submitted to a queue may have different priorities. The indication of priority may be alphanumeric characters (e.g., scale of 1-5, scale of A-N, and/or the like) or based on categories (e.g., urgent, high, medium, low, normal, after hours, and/or the like).

For example, users may be submitting samples to a queue for a selected instrument system that may be shared with other users, and, therefore may already have items present in the queue placed there by other users. Additionally, a user may also have previously placed items in a queue themselves. As new samples arrive and the user generates a sample list for them, when they are submitted for analysis there may be a need to set the priority for them over other items in the queue. Priorities may be set based on instrument system priority and/or priority within a queue. For example, a sample list with an "urgent" priority sample may be added to the top of a queue, interrupting the current sample list (for instance, with a priority below "urgent") but allowing an injection that's in progress to complete before the new item is started. When the "urgent" queue item completes, the queued item it displaced may resume (or the next urgent item).

Figure 7A:
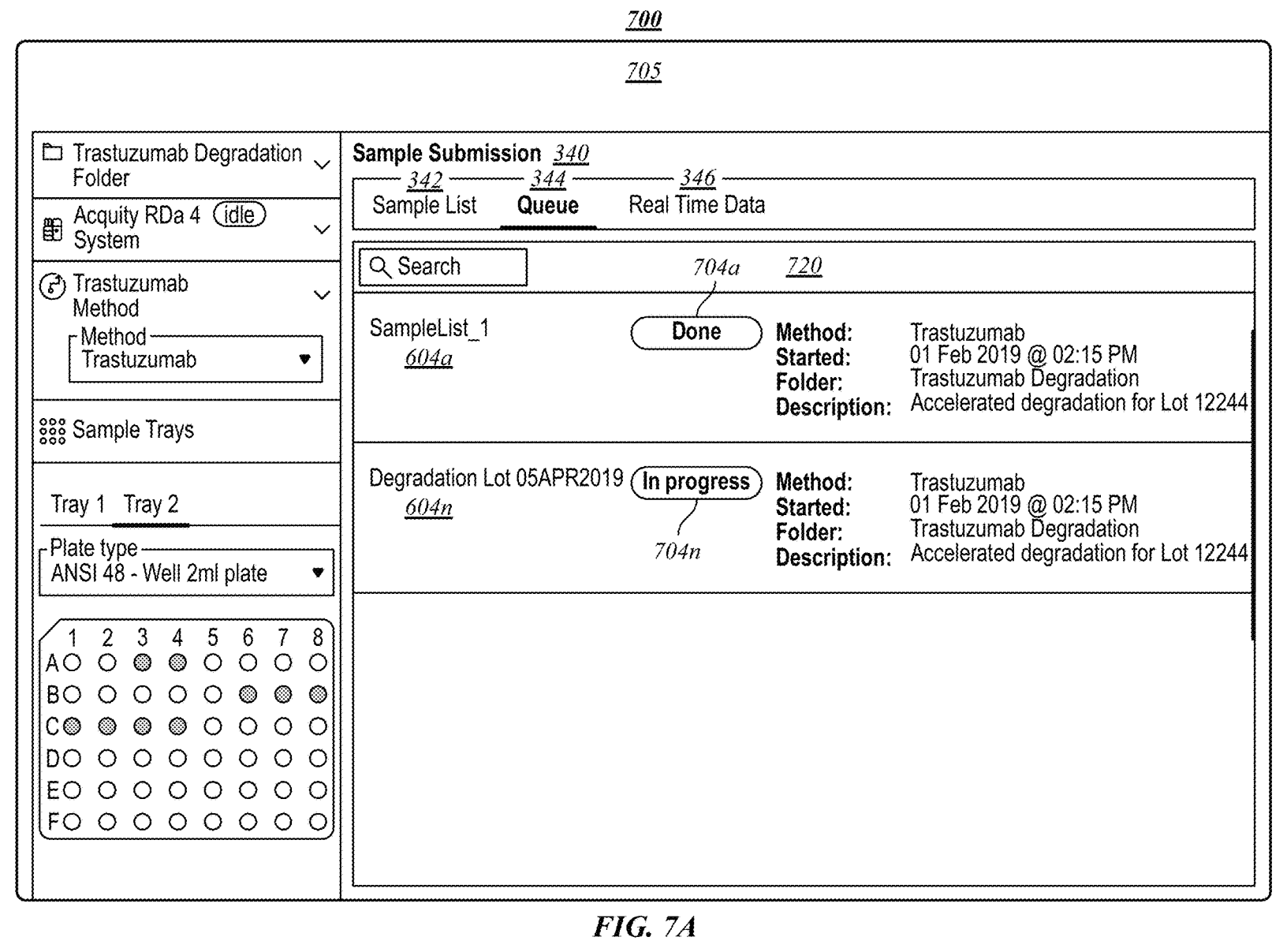
Figure 7B:
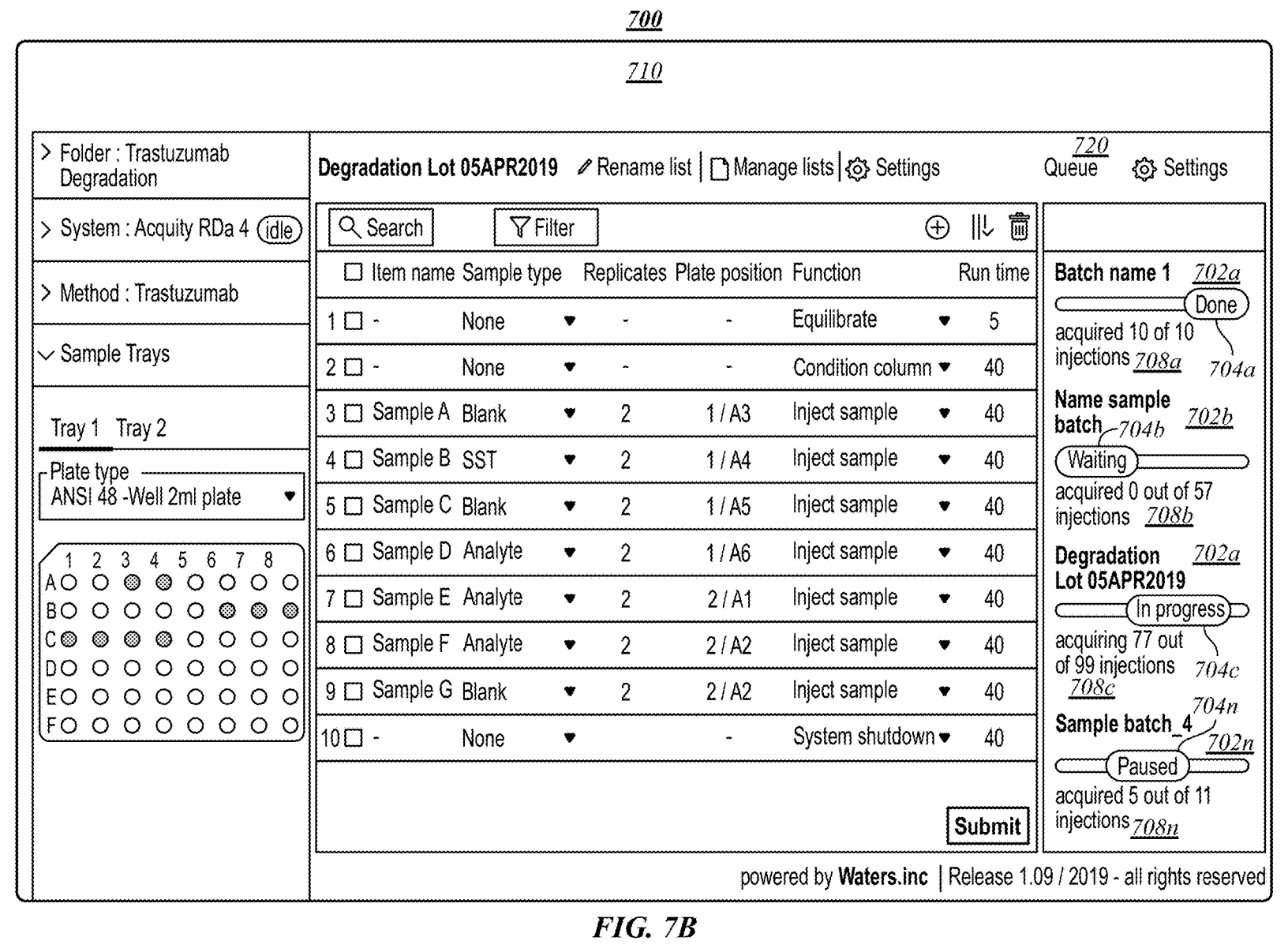
Figure 7F:
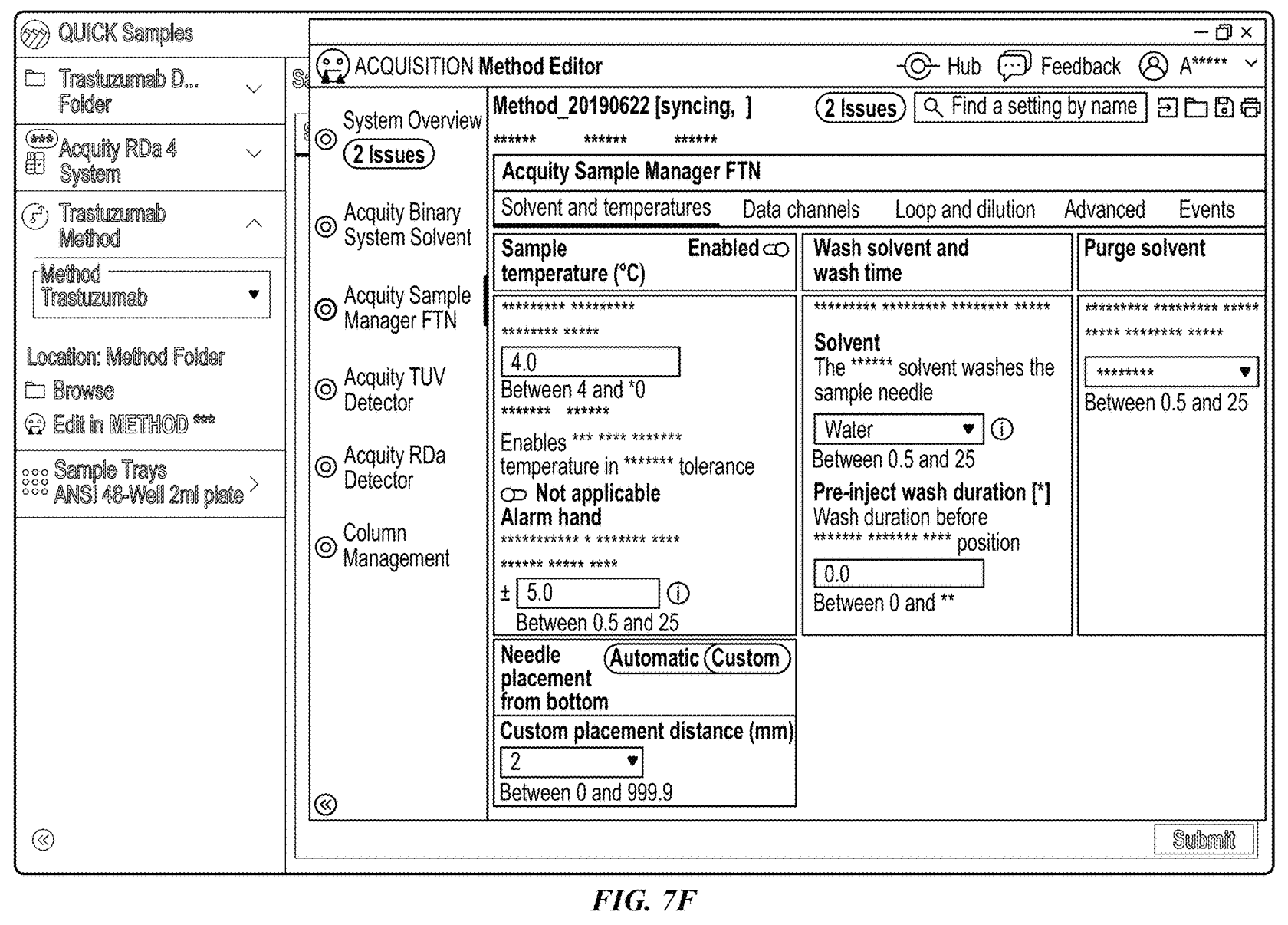
Figure 7G:
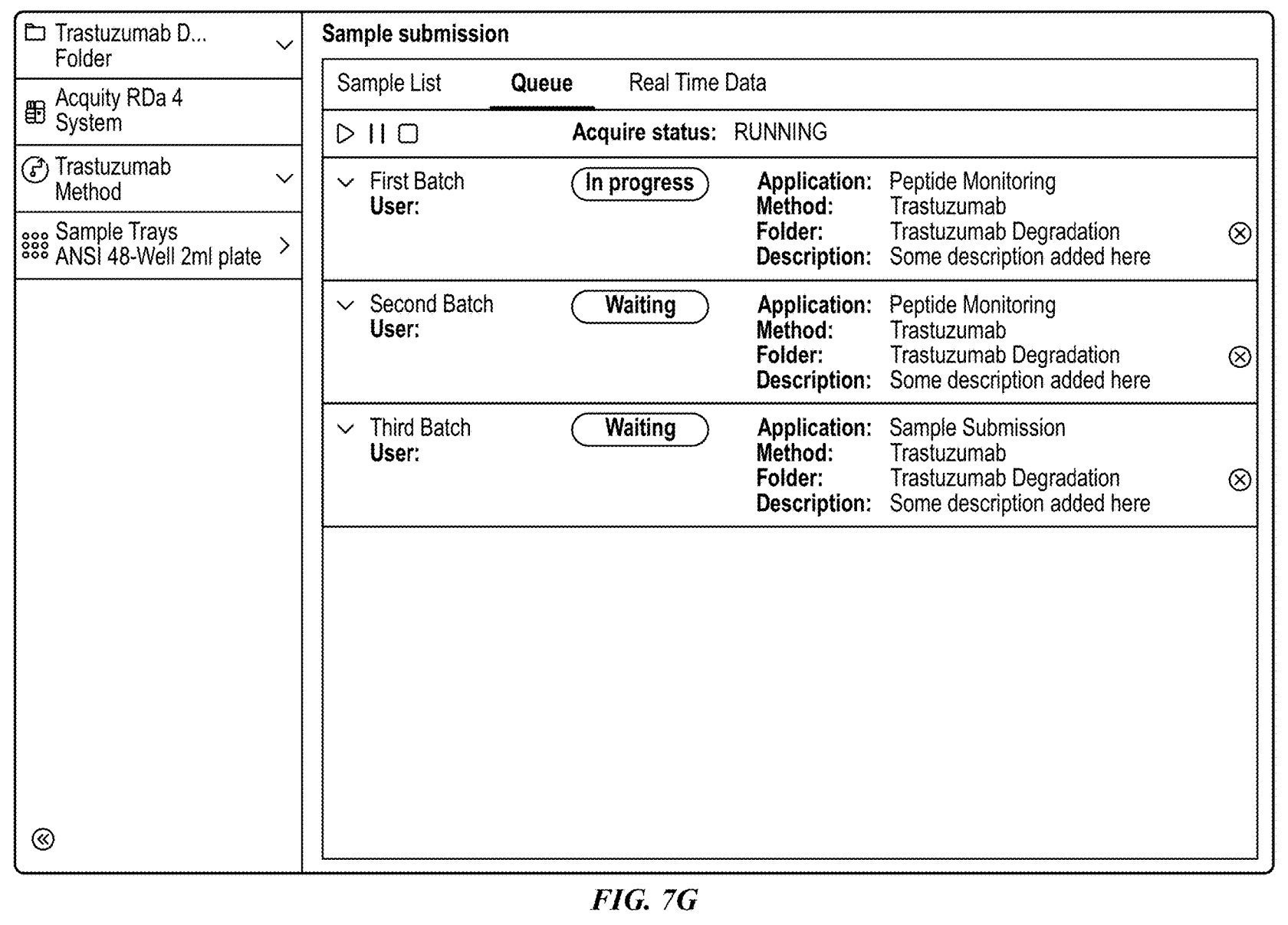

FIGS. 7A-7D illustrates an example of an operating environment 600 that may be representative of some embodiments. More specifically, FIG. 7A depicts analytical services screen 705 with a queue 720 of queue items, such as submitted sample lists 604a-n. In some embodiments, queue 720 may be or may depict a plurality of sample lists 604a-n and their corresponding status 704a-n, such as done, in progress, error condition, and/or the like. In various embodiments, each sample list 604a-n may be associated with sample list information, such as methods, time stamp information, and/or the like.

Referring to FIG. 7B, therein is depicted analytical services screen 710 with a queue 720 according to some embodiments. Queue 720 may include one or more queue elements 702a-n, which may be submitted sample lists, samples, batches (for instance, a batch or collection of injections), and/or the like. Each queue element 702a-n may be associated with a progress object 704a-n operative to graphically indicate a progress of queue element 702a-n, including, for instance, a progress bar indicator and a textual/color indicator. In various embodiments, each queue element 702a-n may include a sample or injection progress indicator 708a-n operative to specifically communicate the progress of individual samples or injections, such as stating the number of injections conducted/remaining.

Referring to FIG. 7C, therein is depicted analytical services screens 715A and 715B with a queue element 702 according to some embodiments. For example, screen 715A may open responsive to selection of a specific queue element 702 on screen 705 and/or 710. In some embodiments, screen 710 may include queue element operations 730, such as selection objects to run, pause, stop and/or the like queue element 702. In some embodiments, a queue element operation 730 may include an object to change the priority of queue element 702. As shown in screen 715B, queue element operations 740 may allow a user to edit a queue element (for instance, a batch, a sample list, a sample, an injection, and/or the like), view injections, delete a queue element, re-order queue elements, and/or the like. In some embodiments, queue information and operations, such as those depicted in FIGS. 7A-7C, may be accessed for a plurality of instrument systems. The ability to modify queues 720 and/or queue elements 702 of other users, instrument systems and/or the like, may be managed via security settings, permissions, user/group profiles, and/or the like. In some embodiments, when a queue element 702 is being modified, its status may be changed, for instance, to "paused."

In general, queue 720 is intended to display work tasks associated with an instrument system or other analytical unit. For example, tasks may be arranged as items or queue elements 702 in queue 720. In some embodiments, each item or queue element 702 may represent a collection or batch of injections. As rows from a sample or injection list are selected and submitted, they may become queue elements 702 in queue 720. In some embodiments, queue 720 may be used by users to view work, for example, that is waiting, completed, in progress, and/or the like an instrument system associated with the current instance of Sample Submission. In this manner, information present in queue 720 may allow a user to, inter alia, assess the quantity of work that has already been presented to an instrument system, for instance, to make decisions, such as if they want to use the current instrument system for their work, or choose another, or choose a different time. In addition, queue 720 may allow users to monitor the progress of each item in queue 720, such as how far a batch has progressed, to provide an estimate of how long it might be before their data is acquired (and optionally processed).

In some embodiments, interfaces associated with queue 720 may allow a user to view items or queue elements 702 that result from submitting rows of a sample list or an injection list for analysis, associate a queue element 702 in the queue 720 with the injection list from which it originated, associate queue elements 702 in queue 720 with the user that submitted them to the queue 720, see the relative order of queue elements 702 in queue 720 for the selected instrument system, see queue elements 702 in queue 720 that belong to them and queue elements 702 that have been placed in the queue 720 by other users (information may differ, e.g., folder to which data are acquiring to), control queue elements 702 (e.g., pause, restart, stop, delete, and/or the like) in queue 720, see the progress of queue elements 702 in queue 720 (e.g., time, progress bar, number of injections, and/or the like), control queue elements 702 in queue 720 that belong to other users (for instance, as governed by permissions, etc.).

In some embodiments, when a sample list is submitted to queue 720, the user may make changes to the associated information. For example, the user may add more samples to a queue element 702 in queue 720, delete samples, change metadata associated with the samples, and/or the like. To visualize and/or determine which injections/data are associated with which sample list or injection list may be provided via a sample set. In some embodiments, a sample set may effectively be an expanded view of a corresponding sample list or injection list that was used to acquire data. Referring to FIG. 7D, therein is depicted sample list 760 and corresponding sample set 765. In some embodiments, sample set 765 may display the injections that will be performed, or that have already been performed as defined by the sample list 760. In various embodiments, sample set 765 may include information regarding date and time of the injections performed to allow replicates, or repeat injections of the same row in sample list 760 to be differentiated from one another.

FIGS. 7E-7Q depict variations of the user interfaces of FIGS. 7A-7D. In particular, these embodiments depict queueing interfaces including play, pause, and stop buttons allowing executing methods to be started, temporarily halted, and terminated, respectively. These interfaces also depict expanded details for each method in the queue.

Figure 8A:
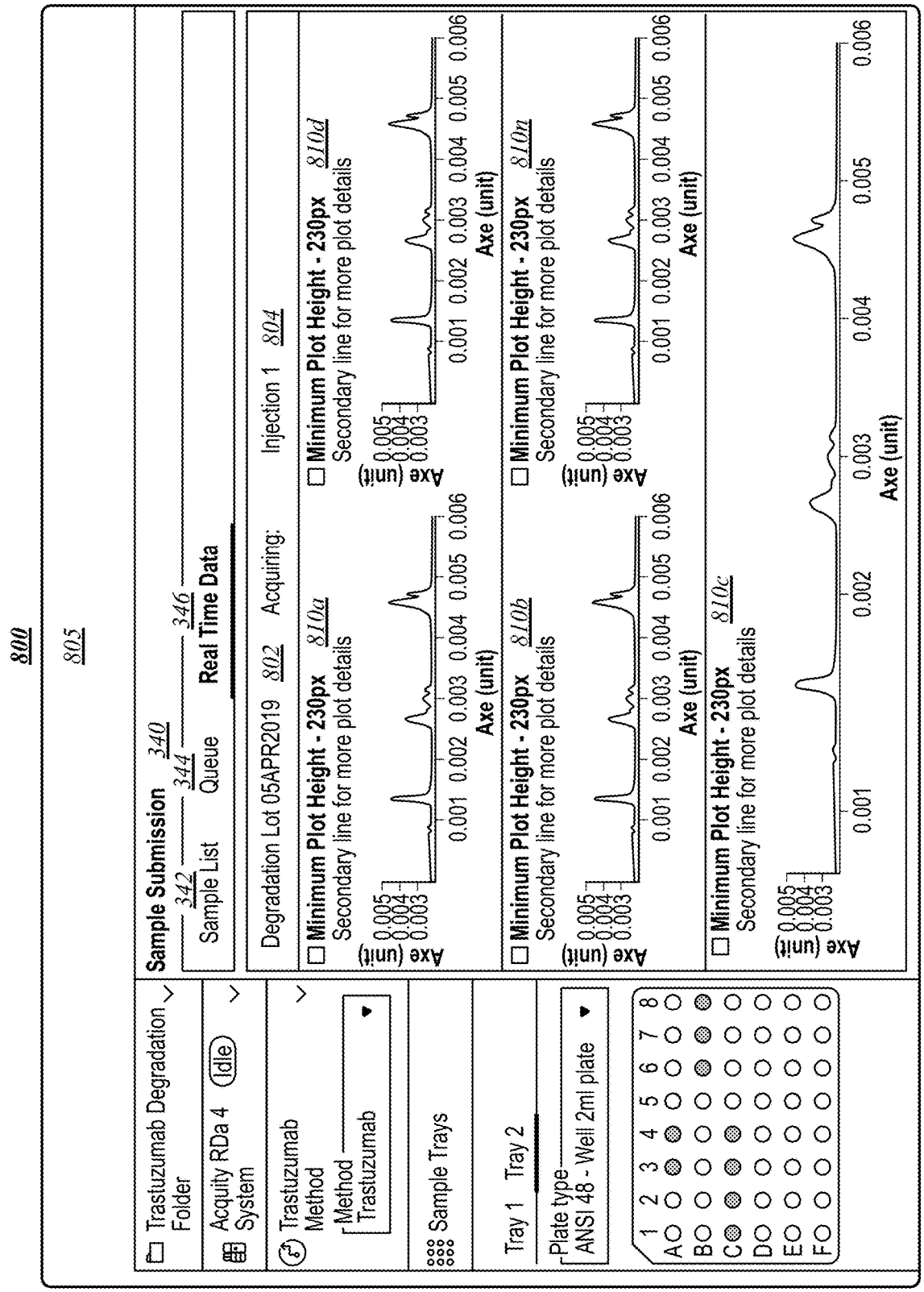
FIGS. 8A-8B illustrates user interfaces according to some embodiments.
Figure 8B:
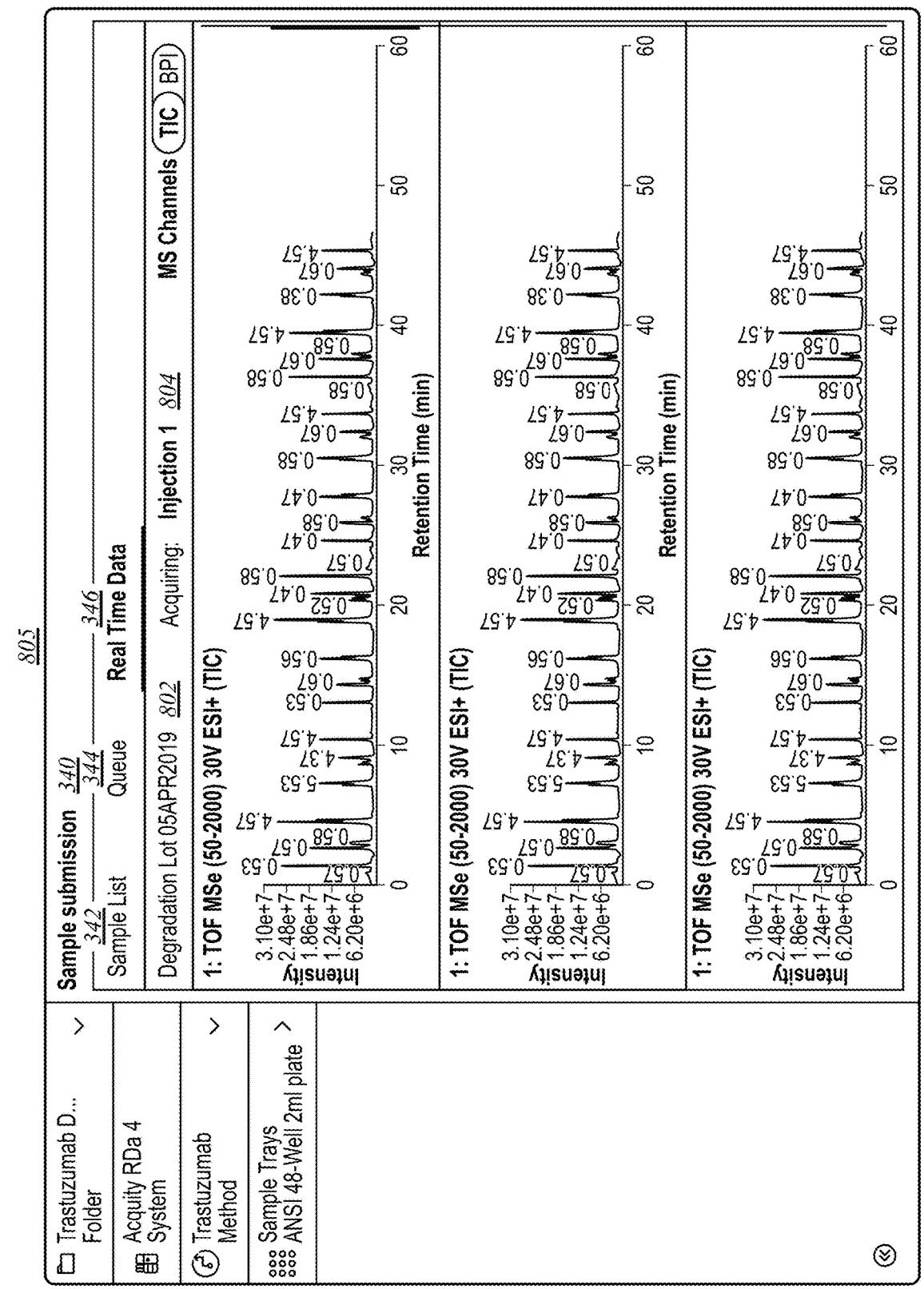

FIGS. 8A-8B illustrate an example of an operating environment 800 that may be representative of some embodiments. More specifically, FIGS. 8A-8B depicts analytical services screen 805 depicting real-time information according to some embodiments, for example, responsive to selection of real-time data object 346. In some embodiments, real-time information screen 805 may operate to allow users to view the real-time or substantially real-time progress of an acquisition, for instance, via data plots 810a-n for a sample list (or batch, injection list, etc.) 802 and/or a particular injection or sample 804. In various embodiments, real-time information screen 805 may, among other things, provide assurance that an instrument system is acquiring data, and appears to be functioning correctly as shown by changes to chromatograms (eluting peaks), spectra, and/or other information. For example, differences from the expected patterns in elution profiles, or the absence of expected peaks in chromatograms/spectra may be identified and allow for user intervention, such as aborting a run, for example. In some embodiments, since there can only be one acquisition in progress, the display of real-time data is independent of the sample or injection list that is displayed.

Non-limiting examples of information presented via analytical services screen 805 may include, for example, for MS, MSe, or other experiments: low and high energy BPI/TIC, spectra low and high energy scans, lockmass channel TIC/BPI, diagnostic channels (e.g., FTN, BSM), chromatograms (acquiring MS/TUV,FLR data), spectra (MS associated with the acquiring MS channels, FLR/TUV), diagnostic plots, and/or the like. In some embodiments, each collection of plots 810a-n may have a channel picker to allow the user to choose from the acquiring channels. In various embodiments, users may be able to hide at least a portion of collections of plots 810a-n, for example, to allow larger plots. In exemplary embodiments, axes on Chromatogram plots may be updated as data are acquired such that the full acquisition range may nit be shown at the start of the run (which may make it difficult to see progress of the run otherwise).

Figure 9:
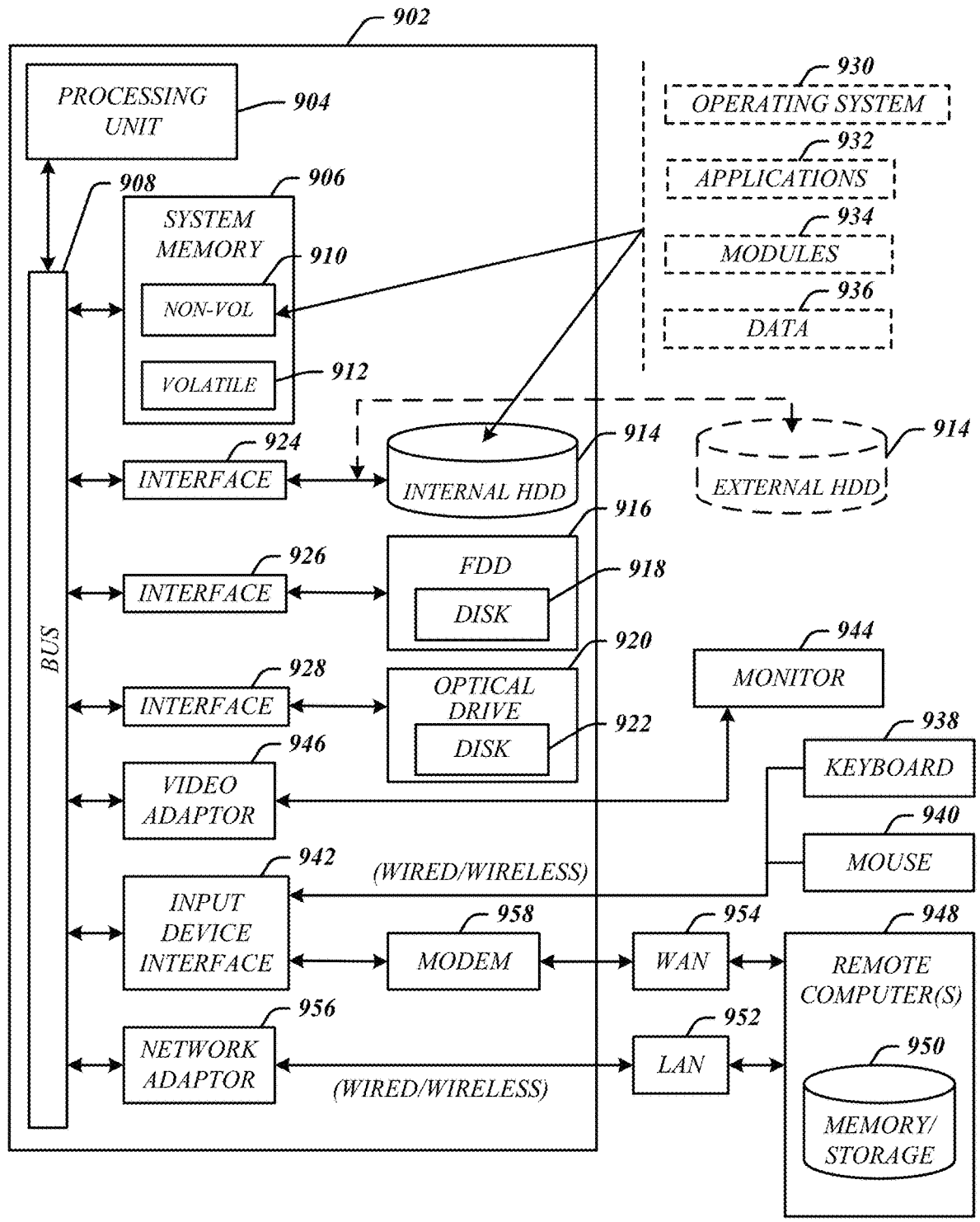
FIG. 9 illustrates an embodiment of a computing architecture.

FIG. 9 illustrates an embodiment of an exemplary computing architecture 900 suitable for implementing various embodiments as previously described. In various embodiments, the computing architecture 900 may comprise or be implemented as part of an electronic device. In some embodiments, the computing architecture 900 may be representative, for example, of computing device 110. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 900. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 900 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 900.

As shown in FIG. 9, the computing architecture 900 comprises a processing unit 904, a system memory 909 and a system bus 909. The processing unit 904 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multiprocessor architectures may also be employed as the processing unit 904.

The system bus 909 provides an interface for system components including, but not limited to, the system memory 909 to the processing unit 904. The system bus 909 can be any of several types of bus structure that may further interconnect to a memory bus (with or without a memory controller), a peripheral bus, and a local bus using any of a variety of commercially available bus architectures. Interface adapters may connect to the system bus 909 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 909 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 9, the system memory 909 can include non-volatile memory 910 and/or volatile memory 912. A basic input/output system (BIOS) can be stored in the non-volatile memory 910.

The computer 902 may include various types of computer-readable storage media in the form of one or more lower speed memory units, including an internal (or external) hard disk drive (HDD) 914, a magnetic floppy disk drive (FDD) 919 to read from or write to a removable magnetic disk 919, and an optical disk drive 920 to read from or write to a removable optical disk 922 (e.g., a CD-ROM or DVD). The HDD 914, FDD 919 and optical disk drive 920 can be connected to the system bus 909 by a HDD interface 924, an FDD interface 929 and an optical drive interface 929, respectively. The HDD interface 924 for external drive implementations can include at least one or both of Universal Serial Bus (USB) and IEEE 1394 interface technologies.

The drives and associated computer-readable media provide volatile and/or nonvolatile storage of data, data structures, computer-executable instructions, and so forth. For example, a number of program modules can be stored in the drives and memory units 910, 912, including an operating system 930, one or more application programs 932, other program modules 934, and program data 939. In one embodiment, the one or more application programs 932, other program modules 934, and program data 939 can include, for example, the various applications and/or components of apparatus 105, 205, 305, and/or 405.

A user can enter commands and information into the computer 902 through one or more wire/wireless input devices, for example, a keyboard 939 and a pointing device, such as a mouse 940. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 904 through an input device interface 942 that is coupled to the system bus 909, but can be connected by other interfaces such as a parallel port, IEEE 1394 serial port, a game port, a USB port, an IR interface, and so forth.

A monitor 944 or other type of display device is also connected to the system bus 909 via an interface, such as a video adaptor 949. The monitor 944 may be internal or external to the computer 802. In addition to the monitor 944, a computer typically includes other peripheral output devices, such as speakers, printers, and so forth.

The computer 902 may operate in a networked environment using logical connections via wire and/or wireless communications to one or more remote computers, such as a remote computer 949. The remote computer 949 can be a workstation, a server computer, a router, a personal computer, portable computer, microprocessor-based entertainment appliance, a peer device or other common network node, and typically includes many or all of the elements described relative to the computer 902, although, for purposes of brevity, only a memory/storage device 950 is illustrated. The logical connections depicted include wire/wireless connectivity to a local area network (LAN) 952 and/or larger networks, for example, a wide area network (WAN) 954. Such LAN and WAN networking environments are commonplace in offices and companies, and facilitate enterprise-wide computer networks, such as intranets, all of which may connect to a global communications network, for example, the Internet.

When used in a LAN networking environment, the computer 902 is connected to the LAN 952 through a wire and/or wireless communication network interface or adaptor 959. The adaptor 959 can facilitate wire and/or wireless communications to the LAN 952, which may also include a wireless access point disposed thereon for communicating with the wireless functionality of the adaptor 959.

When used in a WAN networking environment, the computer 902 can include a modem 959, or is connected to a communications server on the WAN 954, or has other means for establishing communications over the WAN 954, such as by way of the Internet. The modem 959, which can be internal or external and a wire and/or wireless device, connects to the system bus 909 via the input device interface 942. In a networked environment, program modules depicted relative to the computer 902, or portions thereof, can be stored in the remote memory/storage device 950. It will be appreciated that the network connections shown are exemplary and other means of establishing a communications link between the computers can be used.

The computer 902 is operable to communicate with wire and wireless devices or entities using the IEEE 802 family of standards, such as wireless devices operatively disposed in wireless communication (e.g., IEEE 802.19 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A computing device, comprising:
   at least one memory;
   at least one storage device; and
   logic coupled to the at least one memory to perform an installation process, the logic to:
      submit a sample list for acquisition via at least one instrument system, the sample list comprising a plurality of injections for a mass analysis system,
      generate a queue element in a queue for the sample list, the queue element representing the plurality of injections of the sample list to be performed by the at least one instrument system, the queue comprising a plurality of queue elements submitted by a plurality of users and to indicate a progress of each of the plurality of queue elements,
      perform a control function on at least one of the plurality of queue elements responsive to user input, the control function comprising one of stopping, starting, or editing the at least one of the plurality of queue elements, and
      submitting a next queue element of the plurality of queue elements to the at least one instrument system, the submitting configured to cause the at least one instrument system to perform the injection represented by the next queue element.

2. The apparatus of claim 1, the sample list defining different methods for at least two of the plurality of injections.

3. The apparatus of claim 1, the logic to present real-time acquisition information for the plurality of queue elements.

4. The apparatus of claim 1, the logic to present the sample list comprising at least one acquisition indicator responsive to submission of the sample list to the queue, the at least one acquisition indicator indicating samples that have been sent for acquisition or a sample that is currently being acquired.

5. The apparatus of claim 1, the queue associated with an instrument system, the queue comprising the plurality of queue elements for a plurality of users submitting injections to the instrument system.

6. The apparatus of claim 1, the plurality of injections associated with a priority for assigning an order of acquisition within the queue.

7. The apparatus of claim 1, the logic to generate a sample set for the sample list responsive to submission of the sample list to the queue, the sample set indicating injections that have been performed.

8. The apparatus of claim 1, the logic to submit a portion of the sample list, the portion comprising a subset of the plurality of injections.

9. A computer-implemented method comprising, via at least one processor of a computing device:
   submitting a sample list for acquisition via at least one instrument system, the sample list comprising a plurality of injections for a mass analysis system;
   generating a queue element in a queue for the sample list, the queue element representing the plurality of injections of the sample list to be performed by the at least one instrument system, the queue comprising a plurality of queue elements submitted by a plurality of users and to indicate a progress of each of the plurality of queue elements;
   perform a control function on at least one of the plurality of queue elements responsive to user input, the control function comprising one of stopping, starting, or editing the at least one of the plurality of queue elements; and
   submit a next queue element of the plurality of queue elements to the at least one instrument system, the submitting configured to cause the at least one instrument system to perform the injection represented by the next queue element.

10. The computer-implemented method of claim 9, the sample list defining different methods for at least two of the plurality of injections.

11. The computer-implemented method of claim 9, comprising presenting real-time acquisition information for the plurality of queue elements.

12. The computer-implemented method of claim 9, comprising presenting the sample list comprising at least one acquisition indicator responsive to submission of the sample list to the queue, the at least one acquisition indicator indicating samples that have been sent for acquisition or a sample that is currently being acquired.

13. The computer-implemented method of claim 9, the queue associated with an instrument system, the queue comprising the plurality of queue elements for a plurality of users submitting injections to the instrument system.

14. The computer-implemented method of claim 9, the plurality of injections associated with a priority for assigning an order of acquisition within the queue.

15. The computer-implemented method of claim 9, comprising generating a sample set for the sample list responsive to submission of the sample list to the queue, the sample set indicating injections that have been performed.

16. The computer-implemented method of claim 9, comprising submitting a portion of the sample list, the portion comprising a subset of the plurality of injections.

17. A non-transitory computer-readable medium storing instructions that, when executed, cause one or more processors to:

submit a sample list for acquisition via at least one instrument system, the sample list comprising a plurality of injections for a mass analysis system;

generate a queue element in a queue for the sample list, the queue element representing the plurality of injections of the sample list to be performed by the at least one instrument system, the queue comprising a plurality of queue elements submitted by a plurality of users and to indicate a progress of each of the plurality of queue elements;

perform a control function on at least one of the plurality of queue elements responsive to user input, the control function comprising one of stopping, starting, or editing the at least one of the plurality of queue elements; and submit a next queue element of the plurality of queue elements to the at least one instrument system, the submitting configured to cause the at least one instrument system to perform the injection represented by the next queue element.

18. The non-transitory computer-readable medium of claim 17, the sample list defining different methods for at least two of the plurality of injections.

19. The non-transitory computer-readable medium of claim 17, the instructions, when executed, to cause the one or more processors to present real-time acquisition information for the plurality of queue elements.

20. The non-transitory computer-readable medium of claim 17, the instructions, when executed, to cause the one or more processors to submit a portion of the sample list, the portion comprising a subset of the plurality of injections.

* * * * *